US005871710A

United States Patent [19]
Bogdanov et al.

[11] Patent Number: 5,871,710
[45] Date of Patent: Feb. 16, 1999

[54] GRAFT CO-POLYMER ADDUCTS OF PLATINUM (II) COMPOUNDS

[75] Inventors: Alexei Bogdanov, Newton; Ralph Weissleder, Charlestown; Thomas J. Brady, Winchester, all of Mass.

[73] Assignee: The General Hospital Corporation, Boston, Mass.

[21] Appl. No.: 738,177

[22] Filed: Oct. 28, 1996

Related U.S. Application Data

[63] Continuation of Ser. No. 267,150, Jun. 27, 1994, abandoned, which is a continuation-in-part of Ser. No. 250,635, May 27, 1994, Pat. No. 5,593,658, which is a continuation of Ser. No. 940,590, Sep. 4, 1992, abandoned.

[51] Int. Cl.$^6$ .......................... A61K 51/08; A61K 49/00; A61K 31/74; A61K 37/14

[52] U.S. Cl. ...................... 424/1.65; 424/1.69; 424/9.34; 424/9.35; 424/9.36; 424/9.364; 424/78.17; 514/6; 514/54

[58] Field of Search .............................. 424/78, 17, 1.37, 424/1.69, 1.73, 9.323, 9.34, 9.35, 9.6, 9.322, 1.65, 9.36, 9.364; 534/15, 16; 514/6, 54; 530/322, 323, 324, 350, 400

[56] References Cited

U.S. PATENT DOCUMENTS

| | | | |
|---|---|---|---|
| 4,278,660 | 7/1981 | Allcock et al. | 424/78 |
| 4,647,447 | 3/1987 | Gries et al. | 424/9 |
| 4,793,986 | 12/1988 | Serino et al. | 424/1.1 |
| 4,849,208 | 7/1989 | Stavrianopoulos | 424/1.1 |
| 4,921,944 | 5/1990 | Samochocka et al. | 534/10 |
| 4,931,553 | 6/1990 | Gill et al. | 536/121 |
| 4,946,954 | 8/1990 | Talebian et al. | 536/121 |
| 5,024,998 | 6/1991 | Bodor | 514/58 |
| 5,069,216 | 12/1991 | Groman et al. | 128/653.4 |
| 5,091,521 | 2/1992 | Kolar et al. | 536/17.1 |
| 5,094,848 | 3/1992 | Brixter | 424/85.91 |
| 5,141,739 | 8/1992 | Jung et al. | 424/4 |
| 5,160,725 | 11/1992 | Pilgrimm | 424/9 |
| 5,169,933 | 12/1992 | Anderson et al. | 530/391.3 |
| 5,171,563 | 12/1992 | Abrams et al. | 424/1.1 |
| 5,208,324 | 5/1993 | Klaveness et al. | 534/16 |
| 5,213,788 | 5/1993 | Ranney | 424/9 |
| 5,219,564 | 6/1993 | Zalipsky et al. | 424/78.17 |
| 5,252,713 | 10/1993 | Morgan, Jr. et al. | 530/391.7 |
| 5,385,719 | 1/1995 | Unger et al. | 528/272 |
| 5,412,072 | 5/1995 | Sakurai et al. | 530/322 |
| 5,420,105 | 5/1995 | Gustavson et al. | 514/2 |
| 5,501,863 | 3/1996 | Rössling et al. | 424/489 |
| 5,529,775 | 6/1996 | Mikulski et al. | 424/94.6 |
| 5,529,914 | 6/1996 | Hubbell et al. | 435/182 |
| 5,534,542 | 7/1996 | O'Halloran et al. | 514/492 |
| 5,565,215 | 10/1996 | Gref et al. | 424/501 |
| 5,593,658 | 1/1997 | Bogdanov et al. | 424/9.34 |

FOREIGN PATENT DOCUMENTS

| | | |
|---|---|---|
| WO 91/15753 | 10/1991 | WIPO . |
| WO 91/18630 | 12/1991 | WIPO . |
| PCT/US95/07329 | 8/1995 | WIPO . |

OTHER PUBLICATIONS

Yokoyama et al., Makromol. Chem., vol. 190, pp. 2041–2054 (1989).
Duncan et al., Polymers in Medicine, 1984, pp. 51–101.
Abuchowski et al., J. Biol. Chem., 252:3578–81 (1977).
Abuchowski et al., Bioch. Biophy. Acta., 578:41–46 (1979).
Abuchowski et al., J. Biol. Chem., 252:3582–86 (1977).
Abuchowski and Davis, "Soluble Polymer–Enzyme Adducts", Ch. 13, Enzymes as Drugs, (Wiley, New York 1981).
Baxter et al., Invest. Radiol., 26:1035–1040 (1991).
Beauchamp et al., Anal. Biochem., 131:25–33 (1983).
Chazov et al., Throb. Res., 12:809–816 (1978).
Chung-Ja et al., Anal. Biochem., 165:114–127 (1987).
Duewell et al., Invest. Radiol., 25:50–57 (1991).
Fujimoto et al., Cancer, 56:2404–2410 (1985).
Kennady et al., Am. Surg., 33:763–771 (1967).
Manabe et al., Biochem. Biophys. Acta, 883:460–467 (1986).
Nathan et al., Bioconjugate Chem. 4:54–62 (1993).
Sawhey et al., Biomaterials, 13(2):863–79 (1992) Abstract only.
Schmiedl et al., Invest. Radiol., 26:65–70 (1991).
Schumann–Giampieri et al., Invest. Radiol., 26:969–974 (1991).
Torchilin et al., J. Biomed. Mater. Res., 11:223–234 (1977).
Torchilin et al., J. Biom. Mater. Res., 19:461–466 (1985).
Winding, O., Neuroradiol., 21:123–126 (1981).
Wright et al., Radiology, 142:351–354 (1982).
Appleton and Hall, Platinum(II) Complexes with Glycine as an Oxygen–Bound Unidentate Ligand, J. Chem. Soc., Chem. Commun. pp. 911–913, 1983.
Arnon et al., Complexes and Conjugates of CIS–PT for Immunotargeted Chemotherapy, Adv. in Exp. Med. & Biol. 303:79–90, 1991.
Bogdanov et al. A New Macromolecule as a Contrast Agent for MR Angiography: Preparation, Properties, and Animal Studies, Radiology 187:701–706, 1993.
Chao et al., Interaction of CIS Platinum (II) Compounds with Poly(L–Glutamate). A Doubly Anchored Spin–Label and a Doubly Anchored Chromophore–Label, J. of the American Chemical Society 99:24–32, 1977.

(List continued on next page.)

Primary Examiner—John Kight
Assistant Examiner—Lara C. Kelley
Attorney, Agent, or Firm—Fish & Richardson P.C.

[57] ABSTRACT

A biocompatible graft co-polymer adduct including a polymeric carrier, a protective chain linked to the polymeric carrier, a reporter group linked to the carrier or to the carrier and the protective chain, and a reversibly linked Pt(II) compound. The invention also relates to a method of treating a disease in a patient, particularly cancer, by administering to the patient a therapeutically effective amount of the adduct, and may include scanning the patient using an imaging technique which can provide a visible image of the distribution of the adduct.

49 Claims, 14 Drawing Sheets

OTHER PUBLICATIONS

Eastman, The Formation, Isolation and Characterization of DNA Adducts Produced by Anticancer Platinum Complexes, Pharmac. Ther. 34:155–166, 1987.

Ike et al., Controlled Cisplatin Delivery System Using Poly(D,L–Lactic Acid), Biomaterials 13:230–234, 1992.

Kataoka et al., Block Copolymer Micelles as Vehicles for Drug Delivery, J. of Controlled Release 24:119–132, 1993.

Khokhar et al., Synthesis and Antitumor Activity of Ammine/Amine Platinum(II) and (IV) Complexes, J. of Inorganic Biochemistry 51:677–687, 1993.

Maeda et al., Antitumor Activity of a New Series of Platinum Complexes: Trans(±)–1,2–Cyclohexanediammine–Platinum(II) Conjugated to Acid Polysaccharides, Anti–Cancer Drugs 4:167–171, 1993.

Noteborn and Verrijk, Drug Delivery Systems, Current Opinion in Oncology 1:222–230, 1989.

Schechter et al., Blood Levels and Serum Protein Binding of Cis–Platinum(II) Complexed to Carboxymethyl–Dextran, Cancer Chemother. Pharmacol. 24:161–166, 1989.

Schechter et al., Cis–Platinum(II) Complexes of Carboxymethyl–Dextran as Potential Antitumor Agents: Preparation and Characterization, Cancer Biochem. Biophys. 8:277–287, 1986.

Schechter et al., Cis–Platinum(II) Complexes of Carboxymethyl–Dextran as Potential Antitumor Agents: In Vitro and In Vivo Activity, Cancer Biochem. Biophys. 8:289–298, 1986.

Schechter et al., Increased Therapeutic Efficacy of Cis–Platinum Complexes of Poly–L–Glutamic Acid Against a Murine Carcinoma, Int. J. Cancer 39:409–413, 1987.

Schechter et al., Indirect Immunotargeting of Cis–Pt to Human Epidermoid Carcinoma KB Using the Avidin–Biotin System, Int. J. Cancer 48:167–172, 1991.

Schechter et al., Selective Cytotoxicity Against Tumor Cells by Cisplatin Complexed to Antitumor Antibodies Via Carboxymethyl Dextran, Cancer Immunol. Immunother. 25:225–230, 1987.

Sherman and Lippard, Structural Aspects of Platinum Anticancer Drug Interactions with DNA, Chem. Rev. 87:1153–1181, 1987.

Spenlehauer et al., In Vitro and In Vivo Degradation of Poly(D,L Lactide/Glycolide) Type Microspheres Made by Solvent Evaporation Method, Biomaterials 10:557–563, 1989.

Verrijk et al., Polymer–Coated Albumin Microspheres as Carriers for Intravascular Tumour Targeting of Cisplatin, Cancer Chemother. Pharmacol. 29:117–121, 1991.

Verrijk et al., Reduction of Systemic Exposure and Toxicity of Cisplatin by Encapsulation in Poly–Lactide–Co–Glycolide, 52:6653–6656, 1992.

Yokoyama et al., Characterization and Anticancer Activity of the Micelle–Forming Polymeric Anticancer Drug Adriamycin–Conjugated . . . Block Copolymer, Cancer Research 50: 1693–1700, 1990.

Yokoyama et al., Toxicity and Antitumor Activity Against Solid Tumors of Micelle–Forming Polymeric Anticancer Drug and its Extremely Long Circulation in Blood, Cancer Research 51:3229–3236, 1991.

Yolles et al., Timed–Release Depot for Anticancer Agents, J. of Pharmaceutical Sciences 64:115–116, 1975.

Yoshida et al., In Vivo Release of Cisplatin from a Needle–Type Copolymer Formulation Implanted in Rat Kidney, Biomaterials 10:16–22, 1989.

Scheme 1

Scheme 2

Scheme 3

■ - polyaminoacid

⋰⋰⋰ - polyoxyethyleneglycol

● - chelate

⬬ - activated ester

▨ - protective group

GRAFT CO-POLYMER ADDUCTS OF PLATINUM (II) COMPOUNDS

This is a continuation of application Ser. No. 08/267,150, filed Jun. 27, 1994, now abandoned, which is a continuation-in-part of U.S. Ser. No. 08/250,635 filed on May 27, 1994, now U.S. Pat. No. 5,593,658, which is a continuation of U.S. Ser. No. 07/940,590 filed on Sep. 4, 1992 abandoned.

In general, the present invention relates to graft co-polymer adducts which include a platinum (II) compound. The compositions provide for lower toxicity, sustained release and stabilization of platinum (II) compounds, as well as selective delivery to a tumor site.

BACKGROUND OF THE INVENTION
CONTRAST AGENTS FOR MAGNETIC RESONANCE IMAGING

Accurate detection of abnormalities in a patient's body is an essential prerequisite for diagnosing and adequately treating disease. Visualization methods, e.g., magnetic resonance imaging (MRI), are becoming more important for such accurate detection. MRI is non-invasive and requires no exposure of humans to potentially harmful radiation. In MRI, tissues of different origin, such as normal and deviated, e.g., cancerous, tissues, may be differentiated on the basis of differences in relaxation times T1, the spin-lattice or longitudinal relaxation time, or T2, the spin-spin or transverse relaxation time. Because of these differences, differential signal intensity is produced which gives various degrees of contrast in MR images. The greater the difference in T1 or T2, the more pronounced the contrast. However, in many cases diseased or deviated tissue is isointensive, i.e., the diseased or deviated tissue has the same signal intensity as normal tissue, and is therefore not distinguishable from normal tissue without the use of special contrast agents.

Where MR imaging techniques employed to elucidate blood perfusion defects are based on the differentiation of flowing blood from stationary surrounding tissues, e.g., MR angiography (MRA). Three dimensional angiographic techniques, e.g., "Time of Flight" (TOF) and "Phase Contrast" (PC) techniques, provide detailed images of intracranial vessels. However, traditional MRA, i.e., Time of Flight MRA, is dependent on flow velocity and flow shape and thus high-quality angiography of peripheral vessels with high flow resistance is generally impossible due to an effect known as vessel saturation. To overcome this problem, contrast agents have been used to selectively lower the relaxation times of blood.

Gadolinium (III) diethylenetriamine pentaacetic acid (Gd-DTPA) dimeglumine is a widely used contrast agent which is relatively small (MW 538) and extravasates on the first pass through the capillaries. However, the use of Gd-DTPA for MR angiography in all organs except the brain is limited, since the blood half-life of Gd-DTPA is less than 20 minutes, and the biological life in man of GD-DTPA is about 90 minutes. The extravasation results in a rapid decrease in vessel/muscle signal ratio, which makes the accurate detection of abnormalities and disease difficult. Moreover, Gd-DTPA dimeglumine, which is used in clinical practice, is immunogenic, which does not favor its repetitious administration to the same patient.

Similar problems occur with the use of ferrioxamine-B as a contrast agent. In addition, ferrioxamine-B causes a precipitous drop in blood pressure after its intravenous administration.

MRI contrast agents created using natural and synthetic macromolecules offer the advantage of high molecular relaxivity due to the multiple chelating groups coupled to a single polymer backbone. These groups can chelate paramagnetic cations, e.g., in Gd-DTPA-poly-l-lysine, or produce high relaxivity due to the presence of iron oxide, e.g., in iron-containing colloids. However, iron oxide-based colloids have their own ligand-independent specific site of accumulation in the body, e.g., the liver, spleen, and lymphoid tissues.

Chelating groups may be attached to a variety of natural polymers, e.g., proteins and polysaccharides, and synthetic polymers. Chemical attachment, e.g., by conjugation, of DTPA to bovine serum albumin will result in a macromolecular contrast agent, which is suitable for some applications, e.g., NMR-angiography, but because of the efficient recognition of modified albumin by macrophages, and albumin-receptors on endothelial cells this contrast agent has a short blood half-life. It is also immunogenic and toxic to reticuloendothelial system organs. Therefore, use for MR imaging is limited.

One way to diminish the antigenicity of albumin is to mask it with natural and synthetic polymers, e.g., spacer arms, by covalent attachment, but this leaves few reactive groups in the protein globule which are needed for binding the chelates and paramagnetic cations. Therefore, the use of such complexes in MR imaging is limited.

Synthetic polymers of 1-amino acids, such as poly-l-lysine (PL), are an alternative to modified natural proteins as backbones for contrast agents. PL modified with DTPA can be used as a radionuclide carrier for antibody-mediated targeting in nuclear medicine. Poly-l-lysine-DTPA, i.e., poly-l-lysine with DTPA groups bonded to epsilon-amino groups of lysine residues has been suggested as a Gd complexone, i.e., a compound which forms a complex with Gd, for use in MR angiography. It is also known that the toxicity of DTPA-poly-l-lysine is lower than that of DTPA-albumin. However, DTPA-moieties on DTPA-polylysine are recognized by liver Kupffer cells and some kidneys cells, presumably glomerulonephral phagocytes, which cause elevated and relatively rapid removal of the contrast agent from the blood. For example, 90% of the intravenously injected agent, e.g., poly-l-lysine-DTPA(Gd) (MW 48.7 kD), is removed from circulation in 1 hour ($t_{1/2}$=0.134 h) and accumulated in the kidneys, liver, and bone. Moreover, synthesis of DTPA-poly-l-lysine can be carried out with a cross-linking reagent, e.g., cyclic anhydride of DTPA. As a result, it is difficult to avoid the formation of cross-linked products of relatively high molecular weight and the preparation obtained is heterogeneous.

Nitrogen-containing polymers, e.g., polethyleneimine, have been modified with monofunctional derivatives of acetic acid to form a molecule where the backbone nitrogens and acetic acid residues are involved in complex formation with trivalent cations. However, because of extensive undesirable accumulation in the liver, paramagnetic complexes of polyethyleneiminoacetic acid are not widely used in MRI.

Polymeric contrast agents, e.g., starburst dendrimers, constitute a separate family of macromolecules with limited potential value as contrast agents. This family of agents has not been shown to be biocompatible and thus its value for in vivo imaging is limited.

Various polysaccharide-based chelating agents have been previously described; however, their activation complement which has been shown to be a feature of polysaccharides, preclude their extensive use in MR imaging.

Agents with Extended Blood Half-Life

Blood half-life and immunogenicity are crucial characteristics of any contrast agent designed for therapy or medical diagnosis. In some cases, such as enzyme-replacement therapy, fast elimination of therapeutic agents from circulation and accumulation in antigen-presenting cells limit their potential use in the treatment of disease. To overcome this problem, it has been suggested to chemically modify the macromolecular agents, e.g., enzymes, with various natural and synthetic polymers. Dextrans, synthetic polyamino acids, and polyethylene glycols are used most frequently. However, only polyethylene glycol (PEG) and its monomethyl ester (MPEG) are suitable to prolong blood half-life and simultaneously decrease the immunogenicity of the therapeutic agent. The reason for modifying antigenic determinants by MPEG may be explained by the screening of electrostatic charge of the protected micromolecule, e.g., protein, and by the ability to form numerous bonds with water in solutions.

About three molecules of water are associated with each ethylene oxide unit and form the immediately adjacent water microenvironment for the polymer. This prevents, to a great extent, the adsorptive interactions of proteins and cells with PEG chains. The use of PEG in its activated forms, e.g., 4,6-dichloro-s-triazine-activated PEG or MPEG, is undesirable for protein modification, because the activated product is contaminated with by-products and is highly moisture-sensitive. Stable and virtually non-biodegradable bonds have been formed by the conjugation of MPEG, e.g., reacting 4,6-dichloro-s-triazine and 1,1'-carbonyldiimidazole with aminogroups.

PEG and MPEG are used in contrast agents for medical imaging. Covalent modifications of desferrioxamine-B with MPEG improve the body's tolerance of such contrast agents in vivo, but does not result in any significant change in imaging efficacy. Contrast agents containing MPEG or PEG as a component of paramagnetic mixtures or in cross-linked paramagnetic polymers also have been used.

Targeted Contrast Agents

Contrast agents targeted to the sites of interest help to increase the effectiveness of MR imaging methods. Such diagnostic agents may include combinations of a ligand and a paramagnetic contrast agent coupled by strong interaction, e.g., a covalent chemical bond. After systemic application, such a contrast agent accumulates in the target site which is determined by ligand specificity. As a result, the site of accumulation is easily differentiated from surrounding tissue because it appears hyper- (or hypo-) intensive on MR images. The ligand which directs the contrast agent to the target site may be specific to receptors on either normal or transformed cells of a given organ or tissue. In the first case the contrast agent will be accumulated in normal tissue; in the second case, it will be accumulated in altered tissue.

Success in designing a targeted contrast agent is mainly determined by the following properties: 1. avidity to target site; 2. antigenicity, i.e., ability to pass through capillary endothelium; and 3. blood half-life of the ligand or targeting ("vector") molecule. Coupling a contrast agent to a targeting ligand molecule, e.g., an antibody or its fragments, which creates a targeted contrast agent, e.g., a chelated paramagnetic cation, paramagnetic colloid or combination of a chelate and a paramagnetic colloid conjugated to a targeting molecule, typically decreases its potential value for any of a number of reasons, e.g., decreased avidity to a target site, increased antigenicity, or decreased half-life. For example, coupling of a small antibody fragment, e.g., a Fab or Fv chimeric molecule, to a large paramagnetic molecule, e.g., DTPA-polymer, or a superparamagnetic colloid, e.g., iron oxide, to form a targeted contrast agent will increase the immune response of the recipient organism to the agent because of the adjuvant properties of the agent itself. The paramagnetic molecule or colloid itself may be recognized by the recipient organism's opsonizing proteins and the contrast agent may be trapped in reticuloendothelial system organs. As a result, the contrast agent is removed from the circulation by the liver and spleen before any substantial concentration is achieved in the target site. Moreover, such a contrast agent may be recognized as a foreign antigen which may give rise to undesirable host antibodies.

Platinum(II) Compounds

Cis-diaminedichlorplatinum(II) (i.e. cDDP) is a platinum (II) compound which is used to treat bladder, lung, head, neck cervical, testicular and ovarian cancers (Sherman and Lippard, Chem. Rev. 87, 1153 (1987). Other platinum (II) compounds of known or potential therapeutic value include cis-diamminediaquoplatinum (II) (i.e. cis-aq), carboplatin, iproplatin, DACCP, malonatoplatinum, trans (±)-1,2-cyclohexanediammineplatinum(II), cis-DEP, and ammine/amine platinum complexes of the general formula $Pt(II)(NH_3)(RNH_2)Cl_2$, where R is H, methyl, ethyl, isopropyl, cyclopropyl, cyclobutyl, cyclopentyl, or cyclohexyl (see Sherman and Lippard, supra; Schechter, et al. Cancer Immunol. Immunother 25, 225 (1987); Maeda, et al. Anti-Cancer Drugs 4, 167 (1993); Eastman Pharmac. Ther. 34, 155 (1987); Khokar et al. J. Inorganic Chem. 51, 677 (1993)). cDDP and carboplatin are also effective in combination with certain other chemotherapeutic drugs (e.g. doxorubicin, cyclophosphamide) in the treatment of cancer, for example, squamous cell carcinoma, metastatic melanoma, metastatic bladder carcinoma, basal cell carcinoma, and astrocytoma (Physician's Desk Reference pp. 754–757 (1993)). It is generally accepted that the biological target of cDDP is DNA, especially the DNA of rapidly dividing cells such as cancer cells.

The therapeutic value of platinum(II) compounds, particularly cDDP and carboplatin, is generally limited by cumulative nephrotoxicity and renal dysfunction. For example, cDDP toxicity causes nephrotoxicity in 30% of the patients that receive the drug and other adverse reactions have been documented (Physician's Desk Reference, supra). cDDP exhibits a complex pattern of inactivation and elimination from the body, for example, approximately 10% is rapidly removed from the systemic system. A large fraction of the remaining cDDP (>85%) is inactivated by binding with systemic proteins, for example, blood proteins. Therefore, a major clinical problem with the therapuetic administration of cDDP and other platinum (II) compounds is that a large fraction of the drug is rapidly inactivated and eliminated before contacting a tumor.

In addition to direct intravenous administration, other methods of providing cDDP have been proposed. These methods have included sustained release systems involving particulate microspheres and large implants (Verrijk, R. et al., Cancer Res. 52, 6653 (1992); Kyotaini, S. et al., Chem. Pharm. Bull (Tokyo) 40, 2814 (1992); Spenlehauer, G. et al., J. Pharm. Sci. 75, 750 (1986)). Because microspheres generally have a large size (e.g. 20–30 microcentimeters), circulation throughout the body is inhibited. Implants which include cDDP cause severe tissue necrosis (Yoshida, M. et al., Biomaterials 10, 16 (1989)).

Another cDDP delivery system involves administering a non-crosslinked (i.e. linear or branched) homopolymer or co-polymer, combined with cDDP (Maeda, M. et al., Anti- Cancer Drugs 167 (1993); Yoshida M. et al., supra; Schecter, B. et al., Cancer Chemother. Pharmacol. 24, 161 (1989); Schecter B. et al., Int. J. Cancer 39, 409 (1987); Schechter, B. et al., Cancer Biochem. Biophys. 8, 277 (1986); ibid, pg. 289). These systems result in a homopolymeric or co-polymeric adducts which are toxic and do not exhibit desirable solubility.

SUMMARY OF THE INVENTION

The invention features a biocompatible medical composition including a polymeric carrier, a protective chain linked to the polymeric carrier, and a reporter group linked to the carrier or to the carrier and the protective chain. The polymeric carrier may be chosen from the group of polyamino acids, polyethyleneimines, natural saccharides, aminated polysaccharides, aminated oligosaccharides, polyamidoamine, polyacrylic acids, or polyalcohols.

The invention also features a composition having the formula:

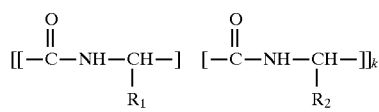

wherein the

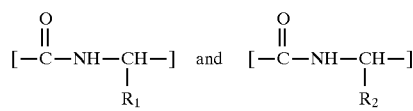

groups can be linked in any order, e.g., the $R_1$ unit can be repeated several times in the chain before an $R_2$ unit occurs, and vice versa; wherein k is 100–560; $R_1$ is $(CH_2)_4NHCO(CH_2)_nCOOCH_2CH_2$-A-B-$OR_3$, where n is 2–6; A is $[OCH_2CH_2]_x$, where x is 15–220; B is $[OCH_2CH_2]_x$ or $[OCH(CH_3)CH_2]_y$, where y+x is 17–220; $R_2$ is a chelating group; and $R_3$ is H, $(CH_2)_yCH_3$ or $(CH_2)_yCOOH$, and p is 0–7.

In this composition, the chelating group may be, e.g., diethylenetriamine pentaacetic acid, 1,4,7,10,-tetraazacyclododecane-N,N',N'',N'''-tetraacetic acid, 1,4,7,10,-tetraazacyclododecane-N,N',N'',-triacetic acid, ethylene-bis(oxy-ethylenenitrilo)tetraacetic acid, or ethylenediaminetetraacetic acid.

The polyamino acid of the composition preferably has 20–560 amino acid units, a molecular weight of 1,000–100,000 daltons, and is preferably non-proteinaceous. The polyamino acid may be a polymer of a single species, or at least two different species of amino acid, or may be a block co-polymer.

The polyamino acid may include polyamino acid fragments linked by cleavable bonds, e.g., S—S bonds. In particular, the polyamino acid may be, e.g., poly-l-lysine, poly-d-lysine, poly-alpha,beta-(2-aminoethyl)-D,L aspartamide, or poly-l-aspartic acid.

The protective chain of the composition may be, e.g., polyethylene glycol, methoxypolyethylene glycol, methoxypolypropylene glycol, a co-polymer of polyethylene glycol, methoxypolyethylene glycol, or methoxypolypropylene glycol, or derivatives thereof. In addition, the protective chain may be a block co-polymer of polyethylene glycol and one of the group of polyamino acids, polysaccharides, polyamidoamines, polyethyleneamines, or polynucleotides. The protective chain may also be a co-polymer of polyethylene glycol including a monoester of a dicarboxylic acid. The protective chain preferably has a molecular weight of 500–10,000 daltons.

The reporter group may be a complexone, e.g., a chelating group. The chelating group may be, e.g., diethylenetriaminepentaacetic acid, triethylenetetramine-hexaacetic acid, ethylenediamine-tetraacetic acid, 1,2-diaminocyclo-hexane-N,N,N',N'-tetra-acetic acid, N,N'-Di(2-hydroxybenzyl) ethylenediamine, N-(2-hydroxy-ethyl) ethylenediaminetriacetic acid, nitrilotriacetic acid, ethylene-bis(oxyethylenenitrilo) tetraacetic acid, 1,4,7,10,-tetraazacyclodo-decane-N,N',N'',N'''-tetraacetic acid, 1,4,7,10,-tetraaza-cyclododecane-N,N',N'',-triacetic acid, 1,4,7-tris (carboxymethyl)-10- (2'-hydroxy)propyl)-1,4,7,10-tetraazocyclodecane, 1,4,7-triazacyclonane-N,N',N''-triacetic acid, or 1,4,8,11-tetraazacyclotetra-decane-N,N', N'',N'''-tetra-acetic acid.

The composition may further include an alfa-, beta-, or gamma-emitting radionuclide linked to the complexone. The radionuclide may be gallium 67, indium 111, technetium 99m, chromium 51, cobalt 57, molibdenium 99, or a molecule linked to an iodine isotope.

The reporter group may also include a diagnostic agent, e.g., a contrast agent, which may include a paramagnetic or superparamagnetic element, or a combination of a paramagnetic element and a radionuclide. The paramagnetic element may be chosen from the group of transitional metals or lanthanides having atomic numbers 21–29, 42, 44, or 57–71. The paramagnetic element may be, e.g., gadolinium (III), dysprosium (III), holmium (III), europium (III), iron (III), or manganese (II).

The invention also features a composition in which the reporter group includes a therapeutic agent such as a cytostatic, antibiotic, hormonal, analgesic, psychotropic, anti-inflammatory, antiviral, or antifungal drug, or a lymphokine.

The composition may further include a targeting group linked to the polymeric carrier or the protective chain or both. The targeting group may be an antibody, fragment of an antibody, chimeric antibody, enzyme, lectin, or saccharide ligand.

The composition may also include a reporter group which is a particle, colloidal particle, or a colloidal precipitate. The colloidal precipitate may include an oxide, sulfide, or hydroxide of a transitional element, or lanthanide having atomic numbers 21–29, 42, 44, or 57–71. The reporter group may also be a silicon oxide colloid or polymer containing silicon, sulfur, or carbon, or a fluorine-containing molecule, e.g., a fluorocarbon.

The reporter group may also be a pyridiyldithioacyl group, e.g., a N-(2-pyridyldithio)propionyl group, N-hydroxysuccinimidyl, N-hydroxysulfosuccinimidyl, imidazolyl, benzotriazolyl, aminoalkyl, aldehyde, thioalkyls, thiolane, haloid acyl, haloid alkyl, or haloid phenyl, or a diazo- or hydrazo-group, e.g., a 4-hydrazionoxyethyl, 4-hydrazino-benzyl, diasirinyl, azidophenyl, or azidoalkyl group.

In addition, the invention features a method of preparing the composition by linking the polymeric carrier with the protective chain to produce a protected carrier, and then linking the protected carrier with the reporter group. If the protective chain includes a methoxypolyethylene glycol analog, linking the polymeric carrier with the analog produces a semi-stable gel. The method may further include linking a targeting group to the carrier, protective group, or both.

The invention also features a method of treating a disease in a patient by administering to the patient a therapeutically or diagnostically effective amount of the composition of the invention. The method may further include scanning the patient using an imaging technique which can detect the reporter group to obtain a visible image of the distribution of the composition. The administration may be by intravascular or intraperitoneal injection, and the imaging technique may be, e.g., magnetic resonance imaging, nuclear medicine imaging, position emission tomography, or single-photon-emission computed tomography.

In particular applicants' composition allows very small dosages of a paramagnetic element, e.g., gadolinium, to be administered to a patient and still obtain excellent images, e.g., MR images. For example, the reporter group may include gadolinium supplied at a dosage of less than 0.05 mmol Gd/kg of body weight of the patient. Preferably, the dosage is about 0.02 to 0.04 mmol Gd/kg of body weight.

The invention also features a method of treating a patient by scanning a submillimeter vessel of the patent to obtain a visible image of the submillimeter vessel. A submillimeter vessel is one that has an inner diameter of less than one millimeter.

The invention also features a biocompatible graft-co-polymer adduct which includes a polymeric carrier, a protective chain linked to the polymeric carrier, and a platinum (II) compound which is reversibly linked to the polymeric carrier or the protective chain or both the polymeric carrier and the protective chain. In an embodiment of the invention, the graft-co-polymer adduct includes a polymeric carrier, a protective chain linked to the polymeric carrier, a reporter group linked to the polymeric carrier or to the carrier and the protective chain and a platinum(II) compound which is reversibly linked to the polymeric carrier or the protective chain or both the polymeric carrier and the protective chain.

Graft-co-polymer adducts of the invention are therapeutic agents which provide dual pharmaceutical action: 1) systemic release of a platinum(II) compound from a graft co-polymer while the adduct circulates in the bloodstream and 2) targeted delivery of a bioactive platinum (II) compound to a tumor. In general, the graft-co-polymer adduct is capable of forming a circulating systemic depot for the sustained release of platinum(II) compounds; the adduct can also be targeted to a tumor. In addition, the graft co-polymer adduct lowers the toxicity of platinum(II) compounds (i.e. as opposed to free drug), by prolonging the biological half-life of the platinum(II) compound as well as protecting the compound from systemic removal and/or inactivation.

The co-polymer of a graft co-polymer is a negatively charged macromolecule which includes a backbone polymer covalently grafted with protective chains;

The backbone polymer of a graft co-polymer is preferably a polyacid, e.g. polyaspartic or polyglutamic acid, polylysine or carboxylated polylysine. A negatively charged polymer is useful since it is capable of forming ionic bonds with aquated platinum (II) compounds. In addition, the protective chain of a graft co-polymer is preferably a polymer of ethylene oxide (poly(ethylene glycol), i.e. PEG or a mono-methoxy ether of poly(ethylene glycol) i.e. MPEG. A protective chain is useful because: 1) it ensures the adduct solubility while maintaining a high drug payload. For example, with cDDP, approximately 30% by weight, or >1 mol cisplatin/per mole carrier of carboxyl groups can be formed; 2) a protective chain assists in the formation of a steric barrier which prevents a platinum(II) compound from binding to molecules in the body, for example, plasma albumin; and 3) a protective chain provides a platinum(II) compound in a form which permits long circulation times (i.e creates a circulating depot). The accumulation of a graft co-polymer platinum(II) compound adduct in a tumor is assisted by the abnormal permeability of tumor vessels.

In a related aspect, the invention features an adduct which includes a polymeric carrier chosen from the group consisting of polyamino acids, preferably non-proteinaceous polyamino acids, polyethyleneimines, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, and carboxymethylated oligosaccharides; where the polyamino acid has 20–560 amino acid residues; the polyamino acid has a molecular weight of 1,000–100,000 daltons; the polyamino acid is a polymer of a single species of amino acid; the polyamino acid is a polymer of at least two different species of amino acids; the polyamino acid is a block co-polymer; the polyamino acid comprises polyamino acid fragments linked by cleavable bonds, preferably S—S bonds; or the polyamino acid is poly-l-lysine, poly-d-lysine, poly-alpha,beta-(2-aminoethyl)-D,L aspartamide, poly-l-aspartic acid or poly-glutamic acid.

In another related aspect, the adduct includes a protective chain which is polyethylene glycol, polypropylene glycol, a co-polymer of polyethylene glycol and polypropylene glycol; or a monoesterified derivative thereof, preferrably methoxypolyethylene glycol, methoxypolypropylene glycol, or a co-polymer of methoxypolyethylene glycol and methoxypolypropyleneglycol; the protective chain is polyethylene glycol monoamine, methoxypolyethylene glycol monoamine, methoxy polyethylene glycol hydrazine, methoxy polyethylene glycol imidazolide or a polyethylene glycol diacid; the protective chain is a block co-polymer of polyethylene glycol and one of the group of polyamino acids, polysaccharides, polyamidoamines, polyethyleneamines, or polynucleotides; the protective chain is a co-polymer of polyethylene glycol comprising a monoester of a dicarboxylic acid; and the protective chain has a molecular weight of 500–10,000 daltons.

In another related aspect, the adduct includes a reporter group. The reporter group is a complexone, such as a chelating group, preferrably the chelating group is diethylenetriamine-pentaacetic acid, triethylenetetramine-hexaacetic acid, ethylenediamine-tetraacetic acid, 1,2-diaminocyclo-hexane-N,N,N',N'-tetra-acetic acid, N,N'-Di (2-hydroxybenzyl)ethylenediamine, N-(2-hydroxyethyl) ethylenediaminetriacetic acid, nitrilotriacetic acid, ethylene-bis(oxyethylene-nitrilo)tetraacetic acid, 1,4,7,10,-tetraazacyclodo-decane-N,N',N'',N'''-tetraacetic acid, 1,4,7, 10,-tetraaza-cyclododecane-N,N',N'',-triacetic acid, 1,4,7-tris(carboxymethyl)-10-(2'-hydroxy)propyl)-1,4,7,10-te traazocyclodecane, 1,4,7-triazacyclonane-N,N',N''-triacetic acid, or 1,4,8,11-tetraazacyclotetradecane-N,N',N'', N'''-tetra-acetic acid; the reporter group includes a diagnostic agent, such as a contrast agent, preferably the contrast agent is a paramagnetic element, preferably the paramagnetic element is chosen from the group of transitional metals or lanthanides having atomic numbers 21–29, 42, 44, or 57–71, preferably gadolinium (III), dysprosium (III), holmium (III), europium (III), iron (III), or manganese (II). The contrast agent can also include a superparamagnetic element.

In another related aspect, the reporter group includes a complexone which includes an alpha-, beta-, or gamma-emitting radionuclide linked to the complexone, preferably the radionuclide is gallium 67, indium 111, technetium 99m, chromium 51, cobalt 57, molibdenum 99, or a molecule linked to an iodine isotope.

In another related aspect, the reporter group includes a therapeutic agent, preferably a cytostatic, antibiotic, hormonal, analgesic, psychotropic, anti-inflammatory, antiviral, or antifungal drug, or a lymphokine; the reporter group is a particle, colloidal particle, or a colloidal precipitate, preferably the colloidal precipitate includes includes an oxide, sulfide, or hydroxide of a transitional element or lanthanide having atomic numbers 21–29, 42, 44, or 57–71; the reporter group is a silicon oxide colloid or polymer containing silicon, sulfur, or carbon; the reporter group has the general formula —COOH or —$(CH_2)_p$COOH, where p is between 1 and 7, inclusive; preferably the reporter group is —$CH_2CH_2$COOH.

In a related aspect, the adduct includes a reversibly linked Pt(II) compound of the general formula:

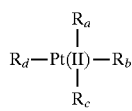

where:

a) each $R_a$, $R_b$, $R_c$, $R_d$ independently is —$OH_2$, Cl, Br, I, —$NH_2$, or —$N(R_e)_2$, where each $R_e$ independently is H, lower alkyl, or lower cycloalkyl, with the proviso that both of $R_e$ are not H; and each $R_a$, $R_b$, $R_c$, and $R_d$ is the same or different;

or b) $R_a$ and $R_d$ are combined to form a linking group of the formula: —$NH(CH_2)_{p2}NH$—, where p2 is 1 or 2; —O—CO—$C(CH_2)_{p3}$—CO—O—, where p3 is between 4 and 6, inclusive;

—NH—$(C_6H_{10})$—NH—; or —O—CO—$(CH_2)_{p4}$—CO—O—, where p4 is between 1 and 6, inclusive; and $R_b$, and $R_c$ are as defined in a);

or c) $R_a$ and $R_d$, $R_b$ and $R_c$, are each independently combined to form a linking group of the formula: —$NH(CH_2)_{p2}NH$—, where p2 is 1 or 2; —O—CO—$C(CH_2)_{p3}$—CO—O—, where p3 is between 4 and 6, inclusive;

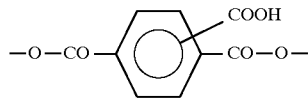

—NH—$(C_6H_{10})$—NH—; or —O—CO—$(CH_2)_{p4}$—CO—O—, where p4 is between 1 and 6, inclusive; and each $R_a$ and $R_d$, $R_b$ and $R_c$, is the same or different.

In a related aspect, the Pt(II) compound is any one of cDDP, cis-aq, carboplatin, iproplatin, DACCP, malonatoplatinum, trans (±)-1,2-cylcohexanediammineplatinum (II), cis-DEP, or Pt(II) $(NH_3)$ $(RNH_2)Cl_2$, where R is H, methyl, ethyl, isopropyl, cyclopropyl, cyclobutyl, cyclopentyl, or cylcohexyl.

In another aspect, the invention features a method of preparing an adduct of the invention, the method including:

a) linking a polymeric carrier with a protective chain to produce a protected carrier; and b) combining a Pt(II) compound with the graft co-polymer in order to form a graft co-polymer adduct, where the adduct includes a reversibly linked Pt(II) compound.

In another aspect, the invention features a method of preparing an adduct of the invention, the method including:

a) linking a polymeric carrier with a protective chain to produce a protected carrier;

b) linking the protected carrier with a reporter group sufficient to form a graft co-polymer; and c) combining a Pt(II) compound with the graft co-polymer in order to form a graft co-polymer adduct, where the adduct includes a reversibly linked Pt(II) compound.

In another aspect, the invention features a method of treating a disease, preferably cancer, in a patient including administering to the patient a therapeutically effective amount of an adduct of the invention.

In preferred embodiments, the method further includes scanning the patient using an imaging technique which can detect a reporter group to obtain a visible image of the distribution of an adduct of the invention; the administration is by intravascular or intraperitoneal injection; the imaging technique is magnetic resonance imaging, nuclear medicine imaging, position emission tomography, or single-photon-emission computed tomography; the cancer is bladder, lung, head, neck, cervical, testicular or ovarian cancer in a human; and the method further includes administering a chemotherapeutic drug, preferably cDDP, carboplatin, doxorubicin or cyclophosphamide.

In related aspect, the invention features an adduct with a reporter group which includes gadolinium supplied at a dosage of less than 0.05 mmol Gd/kg of body weight of the patient.

In another related aspect, the method further includes scanning a submillimeter vessel of the patient to obtain a visible image of the submillimeter vessel.

In another aspect, the invention features a method of selectively accumulating a Pt(II) compound, preferably cDDP or carboplatin in a mammalian tumor, preferably a human tumor, the method including administering an adduct of the invention to the mammal under conditions which allow the adduct to selectively accumulate in the tumor. By "selective accumulation" is meant that the adduct is preferentially concentrated in a tumor rather than surrounding tissues.

In another aspect, the invention features a method of providing a circulating depot of a bioactive Pt(II) compound in a mammal, preferably cDDP or carboplatin provided to a human, the method including administering an adduct of the invention to the mammal in an amount sufficient to provide a circulating depot of the bioactive Pt(II) compound.

In a related aspect, the invention features an adduct which includes between 0.1% and 30% (w\w), inclusive, of platinum, and exhibits a molecular weight of between 50 and 1500 kDa, inclusive.

In a related aspect, the invention features an adduct which includes the graft co-polymer poly[([N-(methoxy of platinum, and exhibits a molecular weight of between 50 and 1500 kDa, inclusive.

In a related aspect, the invention features an adduct which includes the graft co-polymer poly[([N-(methoxy poly (ethylene)glycol)-o-succinyl]-l-lysyl)n-(N-succinyl-l-lysyl) m]]lysine and exhibits a molecular weight of between 1500 and 150,000 daltons, inclusive; where the succinate and the Pt(II) compound, preferably cDDP, are present in a molar ratio of between 1:1 and 1:20 (inclusive), respectively.

In another aspect, the invention features an adduct where the linked polymeric carrier, protective chain and reporter group has the general formula:

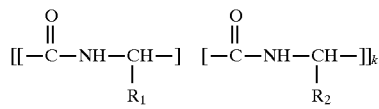

where the

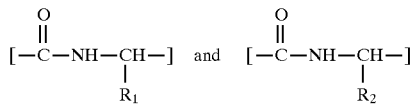

groups can be linked in any order and k is 100–560; and a) $R_1$ is $(CH_2)_4NHCO(CH_2)_nCOOCH_2CH_2A-B-OR_3$, where n is 2–6; A is $[OCH_2CH_2]_x$, where x is 15–220; B is $[OCH_2CH_2]_x$ or $[OCH(CH_3)CH_2]_y$, where y+x is 17–220; $R_2$ is a chelating group; and $R_3$ is H, $(CH_2)_yCH_3$ or $(CH_2)_yCOOH$, where y is 0–7;

or b) $R_1$ is $—CH_2(R_g)NHCO(CH_2)_{n1}COO((CH_2)_{n2}O)_{n3}CH_3$, where $R_g$ is $—CH_2CH_2CH_2—$, $—CO—$ or $—CH_2CO—$, n1 is 2 to 6, inclusive, n2 is 2 or 3, n3 is 10–200, inclusive; and $R_2$ is $—CH_2(R_g)NHCOR_h$, where $R_h$ is $—COOH$ or $—(CH_2)_{y2}COOH$, where y2 is 1 to 7, inclusive.

In a preferred embodiment, the chelating group is diethylenetriamine pentaacetic acid, 1,4,7,10,-tetraazacyclododecane-N,N',N",N'"-tetraacetic acid, 1,4,7,10,-tetraazacyclododecane-N,N',N",-triacetic acid, ethylene-bis(oxyethylenenitrilo)tetraacetic acid, or ethylenediaminetetraacetic acid.

In a related aspect, the invention features an adduct where the reporter group is a pyridiyldithioacyl group, or a diazo- or hydrazo-group, preferably the pyridyldithioacyl group is a N-(2-pyridyldithio)propionyl group, N-hydroxysuccinimidyl, N-hydroxysulfosuccinimidyl, imidazolyl, benzotriazolyl, aminoalkyl, aldehyde, thioalkyls, thiolane, haloid acyl, haloid alkyl, or haloid phenyl; the diazo- or hydrazo-group is 4-hydrazionoxyethyl, 4-hydrazinobenzyl, diasirinyl, azidophenyl, or azidoalkyl groups.

In a final aspect, the invention features an adduct which includes a reporter group which is a fluorine-containing molecule.

As used herein, the term "linked" means covalently or non-covalently bonded, e.g., by hydrogen, ionic, or Van-der-Waals interactions. Such bonds may be formed between at least two of the same or different atoms or ions as a result of a redistribution of electron densities of those atoms or ions.

As used herein, the term "reversibly linked" means a non-covalent bond, e.g., hydrogen, ionic, or Van-der-Waals interactions which stabilizes a Pt(II) compound with a graft co-polymer and which is reversed or dissociated under human physiological conditions in vivo.

A "polymeric carrier" is a molecule comprised of several linked chemical moieties which may be the same or different, and serves as a site where a reporter group is linked and is shielded by protective chains.

A "protective chain" is a molecule(s) which protects a carrier molecule and a reporter group from contact with other macromolecules due to extensive linking of water to the chains.

A "complexone" is a molecule or several molecules or chemical radicals or moieties which constitute a favorable environment for linking an ion (a cation or an anion). Dissociation of the ion from the environment is hindered due to kinetic or/and thermodynamic stability of linking.

A "chelating molecule" or "chelate" is a complexone which links cations.

A "reporter group" as used herein is a non-traditional definition which includes an atom, ion, molecule, or complexone that may be linked to a polymeric carrier or protective chain and which can be detected by any methods disclosed herein. A reporter group may be a therapeutic or diagnostic agent.

The terms "derivative" or "analog" as used herein mean a compound whose core structure is the same as, or closely resembes that of, a parent compound, but which has a chemical or physical modifaction, such as a different or additional side groups; the term inclues co-polymers of parent compounds that can be linked to other atoms or molecules.

The terms "ligand", "targeting group", or "vector molecule" mean any atom, ion, or molecule linked to a carrier and/or to a protective chain and/or to a reporter group to increase the accumulation of the composition in a target site of an organism to a greater degree through the targeting group were absent.

The term "polyamino acid fragment" means individual amino acid radicals or several linked amino acids which may be linked to form a polyamino acid.

A "semi-stable gel" is a gel which forms a liquid phase by standing, or when temperature, pH or other conditions are varied.

The term "vessel mapping" refers to obtaining an image of a vessel or vessels where spatial orientation and delineation of vessels may be elucidated.

The term "aminated" describes molecules including linked amino groups.

A "diagnostically effective amount" of the composition is an amount that will provide an image of the composition in the patient.

A "therapeutically effective amount" of the composition is an amount that will provide a therapeutic benefit to the patient.

A "lower alkyl", as used herein, is a branched or straight chain hydrocarbon of between 1 and 6 carbon atoms, inclusive.

A "lower cycloalkyl", as used herein, is a cyclic hydrocarbon of between 4 and 6 carbon atoms, inclusive.

A bioactive Pt(II) compound, as used herein, is a Pt(II) compound, either free or reversibly linked with an adduct of the invention, which is capable of forming one or more covalent linkages with DNA under human physiological conditions in vivo.

Some important features of the compositions of this invention which make them surprisingly suitable for MR imaging include: 1) the ability to chelate paramagnetic cations to achieve a high molecular relaxivity, which is essential for its use as an NMR contrast agent 2) an extended blood half-life 3) low toxicity and 4) non-immunogenicity.

This invention also provides the advantages of only having to administer one dose of the contrast agent, along with enhanced signal/noise ratios in the diagnostic images obtained.

The following properties are common for the compositions of the invention: 1) increased relaxivity of each paramagnetic cation compared to Gd-DTPA, 2) large numbers of chelating groups on each molecule, 3) enhanced blood pool concentration after intravenous injection, 4) enhanced sites of abnormal endothelial permeability, and 5) prolonged circulation time compared to Gd-DTPA.

Other features and advantages of the invention will be apparent from the following description of the preferred embodiments and from the claims.

DETAILED DESCRIPTION

The drawings are first briefly described. Drawings

Figure 13A:
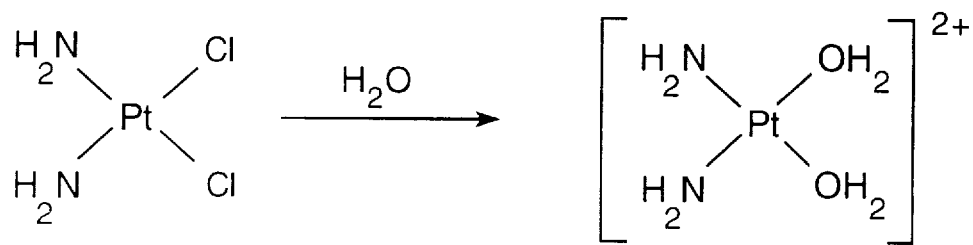
Figure 13B:
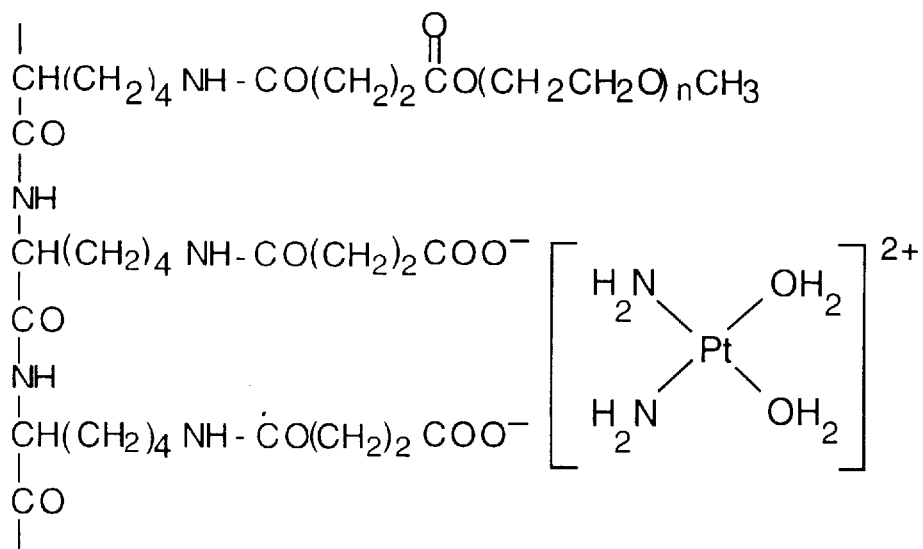

FIGS. 13A and 13B are a drawing showing a reversible linkage between a cis-aq molecule and a portion of the graft-co-polymer. The reversible linkage is an ionic (i.e., electrostatic) interaction between the cis-aq molecule and the graft co-polymer. Part I outlines the hydration of cDDP resulting in the formation of cis-aq. Part 2 shows the electrostatic interaction between cis-aq and the graft co-polymer.

Figure 14:
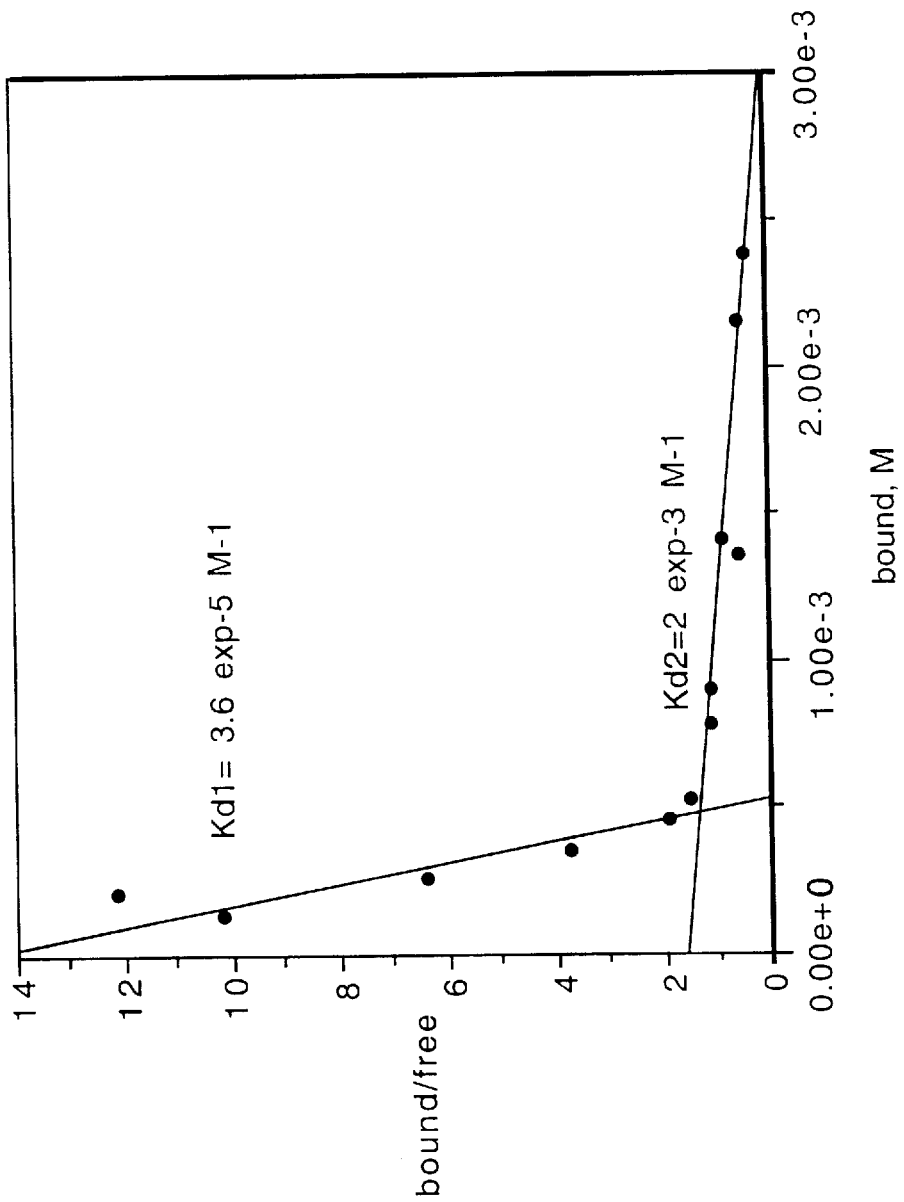

FIG. 14 is a graph showing the binding of cDDP to MPEG-PL-succinate as determined by HPLC quantitative analysis. The graph is presented in Scatchard coordinates.

Figure 15:
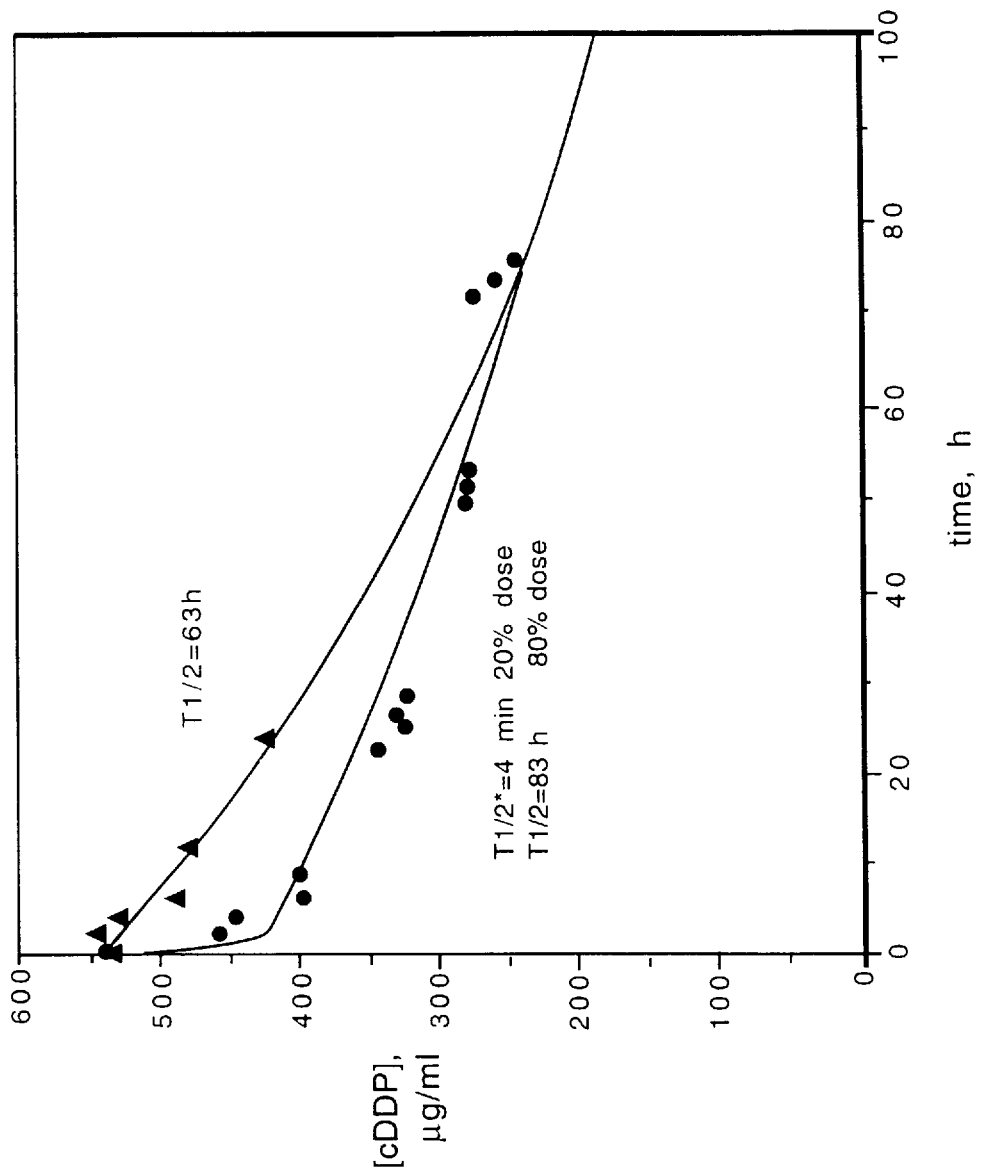

FIG. 15 is a graph showing the time dependent release of cDDP from the adduct MPEG-Poly(L-Lys)succinate/cDDP in the presence of saline (triangles) or bovine serum albumin (i.e. BSA) (circles).

Figure 16:
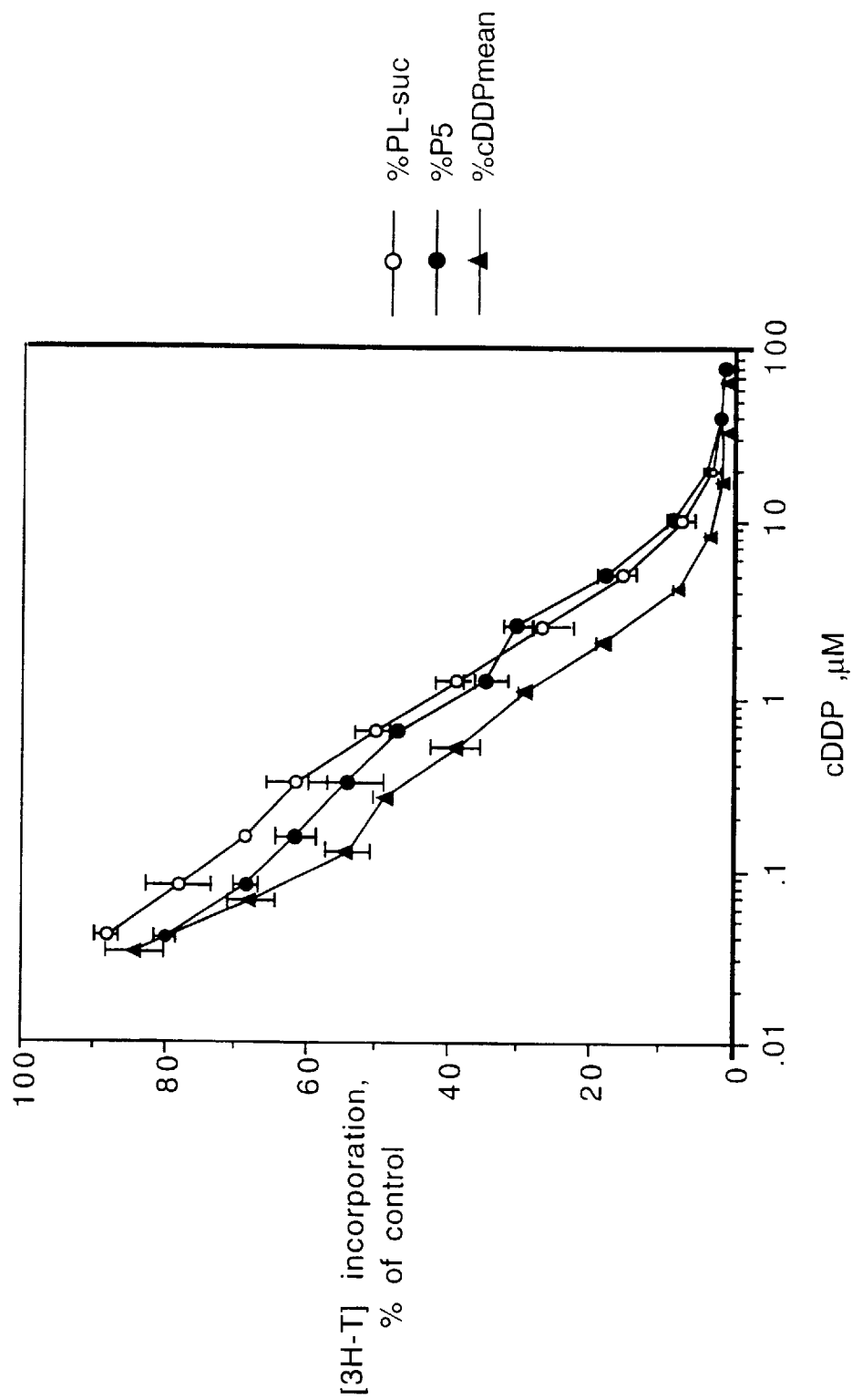
Figure 17A:
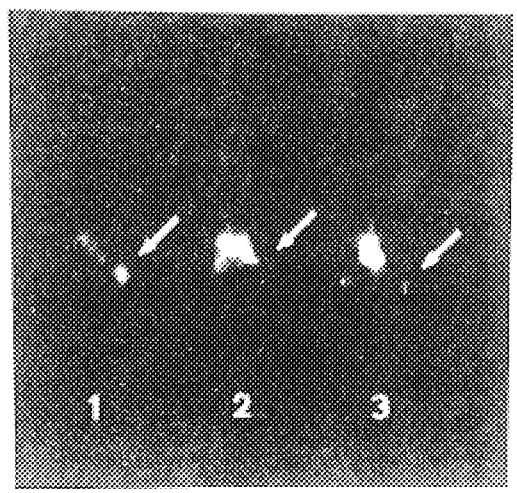
Figure 17C:
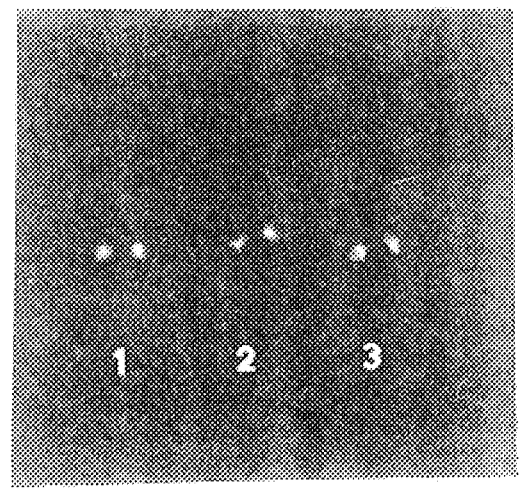
Figure 17B:
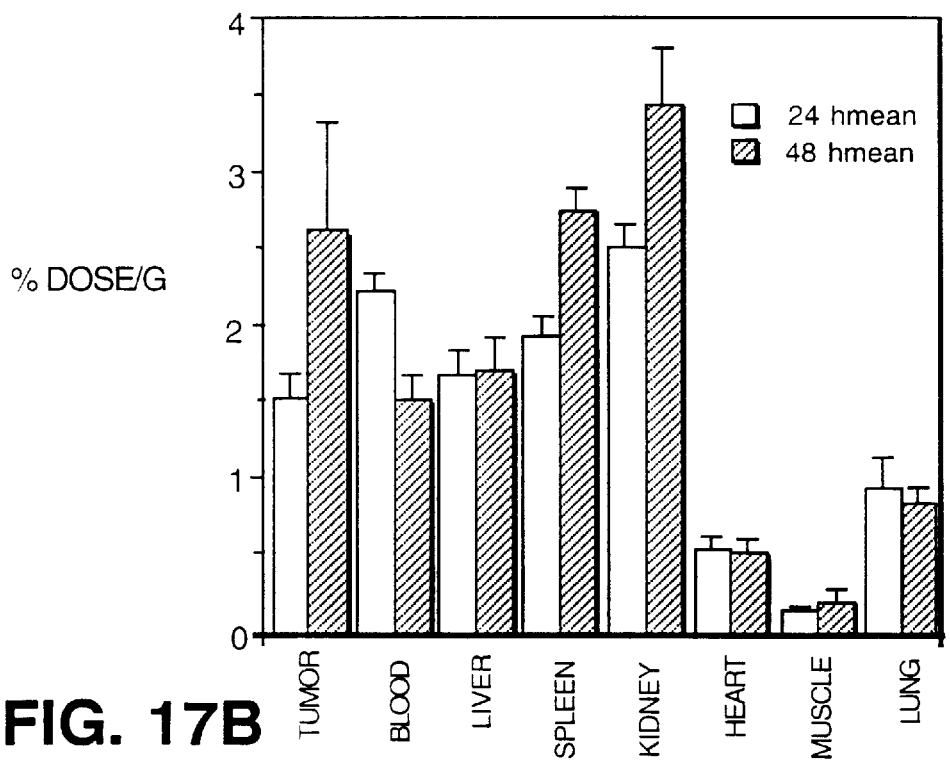
Figure 17D:
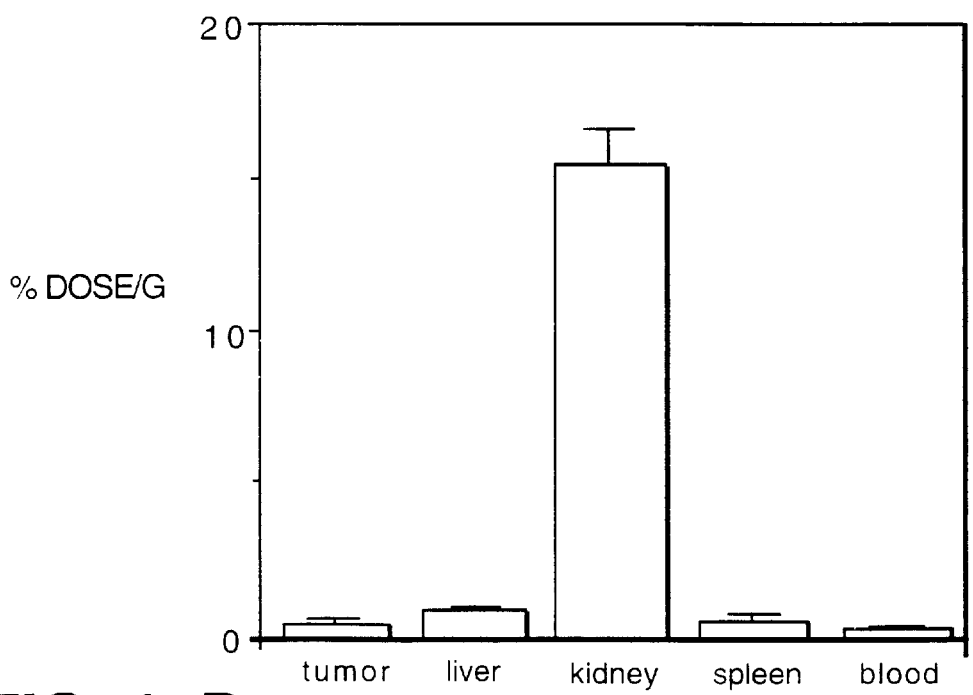

FIG. 16 is a graph showing the inhibition of DNA synthesis in BT-20 cells after the administration of the graft co-polymer adduct MPEG-Poly(L-Lysine)-succinate/cDDP (closed circles), or Poly(L-Lys)-succinate/cDDP (open circles) or free cDDP (triangles). Results presented are presented as the mean±SD (n=3).

FIG. 17 is a pictorial (Panels A and C) and graphical (Panels B and D) representation of the biodistribution of the graft co-polymer adduct MPEG-Poly(L-lysine) succinate/cDDP in NF13762-adenocarcinoma-bearing Fisher rats. The distribution of MPEG-Poly(L-Lys)-succinate/cDDP (Panels A and B) and Poly(L-Lys)-succinate (Panels C and D) in NF13762-adenocarcinoma-bearing Fisher rats is shown after 24 hr (solid bars, Panel B), 48 hr (hatched bars, Panel B) and 48 hr (Panel D). Panel A and C show gamma camera images. Panels B and D show the biodistribution data which is presented as mean±SD (n=3 animals). Images were obtained with [$^{111}$In]-DTPA labeled polymers. Arrows indicate the selective accumulation of the MPEG-Poly(L-lysine) succinate/cDDP adduct in the tumor site.

The compositions of this invention include a polymeric carrier, a protective chain linked to polymeric carrier, and, optionally, a reporter group. For example, the graft co-polymer may have the following formula:

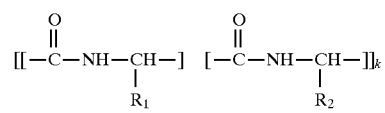

where the

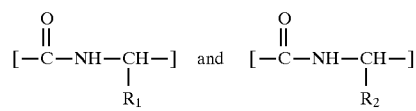

groups can be linked in any order and k is 100–560; and a) $R_1$ is $(CH_2)_4NHCO(CH_2)_nCOOCH_2CH_2A\text{-}B\text{-}OR_3$, where n is 2–6; A is $[OCH_2CH_2]_x$, where x is 15–220; B is $[OCH_2CH_2]_x$, or $[OCH(CH_3)CH_2]_y$, where y+x is 17–220; $R_2$ is a chelating group; and $R_3$ is H, $(CH_2)_yCH_3$ or $(CH_2)_yCOOH$, where y is 0–7;

or b) $R_1$ is $-CH_2(R_g)NHCO(CH_2)_{n1}COO((CH_2)_{n2}O)_{n3}CH_3$, where $R_g$ is $-CH_2CH_2CH_2-$, $-CO-$ or $-CH_2CO-$; n1 is 2 to 6, inclusive; n2 is 2 or 3; n3 is 10–200, inclusive; and $R_2$ is $-CH_2(R_g)NHCOR_h$, where $R_h$ is $-COOH$ or $-(CH_2)_{y2}COOH$, where y2 is 1 to 7, inclusive.

Polymeric carriers

The polymeric carrier may be chosen from synthetic, non-proteinaceious polyamino acids, e.g., a linear, linked or branched polymer of a single amino acid species or of different amino acid species, e.g., regular or statistic block-co-polymers of polyamino acids, e.g, preferably linear poly-l- or poly-d-lysine, carboxylated or carboxymethylated poly-alpha, beta-(2-aminoethyl)-d,l-aspartamide, poly-l-aspartic acid, or poly-glutamic acid. The molecular weight of the polyamino acid carrier is preferably between 1,000 and 100,000 Daltons. Polyamino acids with narrow molecular weight (MW) distributions are preferred to those with broad MW distributions. The polyamino acids are linked with peptide bonds or, when obtained by condensation of two or more polyamino acid fragments or individual amino acids with cleaveable bonds, e.g., S—S bonds, which may be cleaved in vivo. Polyamino acids may be prepared by chemical synthesis or by recombinant techniques, such as genetic engineering.

The polymeric carrier also may include polyethyleneimines, e.g., branched amino-containing polymers or carboxylated polyethyleneimines, i.e., reacted with derivatives of carbonic acids; natural saccharides containing amino acids or carboxylic acids, e.g., galacturonic acid, glucuronic acid, mannuronic acid, hyaluronic acid, pectic acid, neuraminic acid, alginic acid, carrageenan; aminated, e.g. including linked amino groups, polysaccharides or oligosaccharides (linear or branched); or carboxylated, carboxymethylated, sulfated or phosphorylated polysaccharides or oligosaccharides, e.g., reacted with derivatives of carbonic, dicarbonic, sulfuric, aminosulfuric, or phosphoric acids with resultant linking of carboxylic, aminocarboxylic, carboxymethyl, sulfuric, amino or phosphate groups. Such oligosaccharides may be obtained by chemical alteration of, e.g., dextran, mannan, xylan, pullulan, cellulose, chytosan, agarose, fucoidan, galactan, arabinan, fructan, fucan, chitin, pustulan, levan or pectin. In addition these polysaccharides or oligosaccharides may be heteropolymers or homopolymers of monosaccharides, e.g., glucose, galactose, mannose, galactose, deoxyglucose, ribose, deoxyribose, arabinose, fucose, xylose, xylulose, or ribulose.

The polymeric carrier may be a linear, branched or dendrimeric polyamidoamine; polyacrylic acid; polyalcohols, e.g., polyvinylalcohol and polyxylitol to which carboxylic or amino groups are chemically linked; or oligonucleotides.

Protective Chains

The protective chain may be poly(ethylene glycol) (i.e. PEG), preferably the PEG is esterified by dicarboxylic acid to form a polyethylene glycol monoester; for example, methoxy poly(ethylene glycol) (i.e. MPEG) or a copolymer of poly(ethylene glycol) and poly(propylene glycol), preferably in a form of an ester with a dicarboxylic acid; methoxypolypropylene glycol; polyethylene glycol-diacid; polyethylene glycol monoamine; MPEG monoamine; MPEG hydrazide; or MPEG imidazolide, and derivatives of all of the above.

In addition, the protective chain may be a block-copolymer of PEG and another polymer, e.g., a polyamino acid, polysaccharide, polyamidoamine, polyethyleneamine or a polynucleotide (as described above under polymeric carriers). The blocks are preferably alternated to give a linear block-co-polymer. The overall molecular weight of the protective chain is 500 to 10,000 daltons, inclusive. The protective chain is preferably linked to the polymeric carrier by a single bond.

Reporter groups

The reporter groups of the invention are preferably linked to a polymeric carrier but also may be linked to a protective chain. The reporter groups include complexones, e.g., chelating molecules such as
diethylenetriamine-pentaacetic acid (DTPA),
triethylenetetraminehexaacetic acid (TTHA),
ethylenediaminetetraacetic acid (EDTA),
1,2-diaminocyclohexane-N,N,N',N'-tetraacetic acid,
N,N'-Di(2-hydroxybenzyl)ethylenediamine (HBED),
N-(2-hydroxyethyl)ethylenediaminetriacetic acid,
nitrilotriacetic acid,
ethylene-bis(oxyethylenenitrilo)tetraacetic acid (EGTA),
1,4,7,10,-tetraazacyclododecane-N,N',N'',N'''-tetraacetic acid (DOTA),
1,4,7,10,-tetraazacyclododecane-N,N',N'',-triacetic acid (DO3A),
1,4,7-tris(carboxymethyl)-10-(2'-hydroxy)propyl)-1,4,7,10-tetraazocyclodecane (HP-DO3A),
1,4,7-triazacyclonane-N,N',N''-triacetic acid (NOTA),
1,4,8,11-tetraazacyclotetradecane-N,N',N'',N'''-tetraacetic acid (TETA), preferably DOTA and DTPA, where these chelating molecules preferably include a contrast agent, e.g., a paramagnetic cation and/or radionuclide.

The paramagnetic elements, e.g., cations, include transitional metals or lanthanides, e.g. elements with atomic numbers 21–29, 42, 44, 57–71, preferably gadolinium (III), dysprosium (III), holmium (III), europium (III), iron (III), or manganese (II).

The radionuclides include alfa-,beta- and gamma-emitters, preferably gallium 67, indium 111, technetium 99m, chromium 51, cobalt 57, molibdenium 99, molecules, e.g., tyrosine and p-oxybenzoic acid, linked to isotopes of iodine, e.g., iodine 131.

The reporter group may also include fluorine-containing molecules, e.g., fluorocarbons.

The reporter group may also include therapeutic agents, e.g., cytostatics, antibiotics, hormones, e.g., growth factor, analgesics, psychotropic, antiinflammatory, antiviral, antifungal drugs or lymphokines, e.g., interleukin 2. The therapeutic agents are preferably linked to a carrier with detachable or semistable bonds.

The reporter group may also include a particle, or colloidal particle, or colloidal precipitate of oxides, sulfides and/or hydroxides of transitional elements and lanthanides with atomic numbers 21–29, 42, 44, 57–71, or silicon oxide colloids or polymers containing silicon or polymers of atoms of sulfur, carbon, or silicon. The particle or particles may be contained as an integral part of, or may be surrounded by, a semi-permeable membrane.

The compositions may also include additional reporter groups which may be chosen from $(CH2)_pCOOH$, where p is between 0 and 7, inclusive; pyridyldithioacyl groups, e.g., N-(2-pyridyldithio)propionyl groups; N-hydroxysuccinimidyl, N-hydroxysulfosuccinimidyl, imidazolyl, benzotriazolyl, aminoalkyl, aminoacyl, aldehyde, thioalkyls, thiolanes, haloid acyl, haloid alkyl, or haloid phenyl; diazo- and hydrazo-, e.g. 4-hydrazinoxyethyl, 4-hydrazinobenzyl, diazirinyl, azidophenyl, or azidoalkyl groups.

The above groups are linked to the polymeric carrier and/or to the protective chains, and are needed for conjugating or linking other ligands, e.g., a targeting group, capable of interacting with cell surface receptors, proteoglycans, adhesion molecules, ion channels or enzymes, to the compositions of this invention.

Targeting Group

The targeting group may include antibodies; fragments of antibodies; chimeric antibodies, where said antibodies are polyclonal or monoclonal; enzymes; quasi substrates of enzymes; lectins; or saccharide ligands of lectins detachably or nondetachably linked to the composition.

Synthesis of the composition

Figure 1:
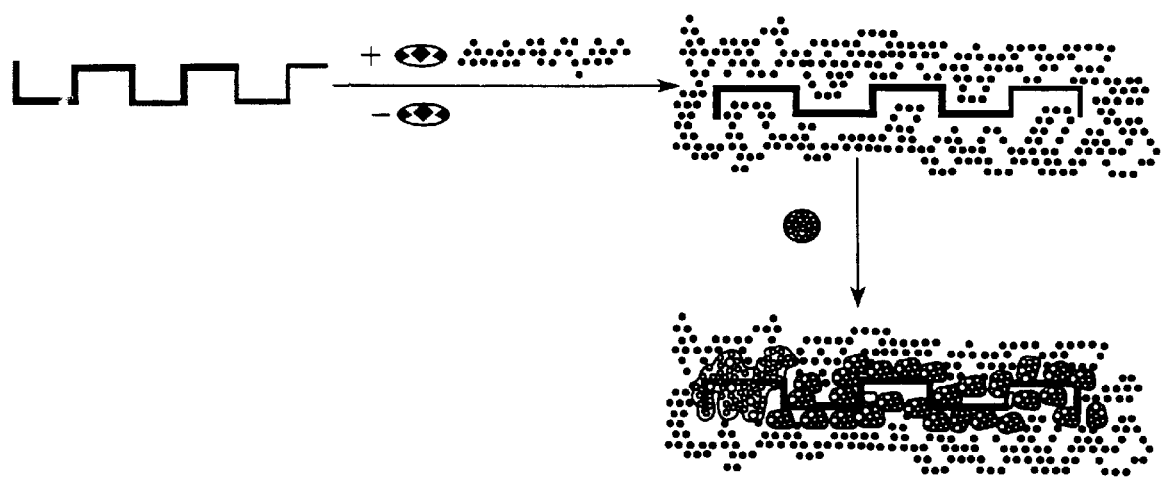
FIG. 1 is a diagram of three schemes for synthesizing the compositions of the invention.
Figure 1:
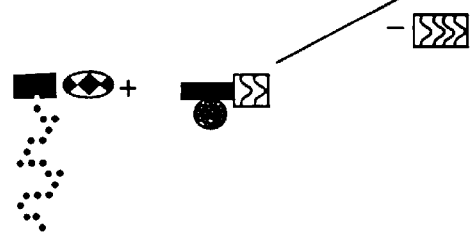
Figure 1:
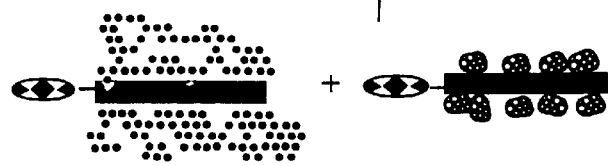

The compositions of this invention may be synthesized using any one of the following methods (See FIG. 1). An example of synthesis using poly-l-lysine as a polymeric carrier, MPEG as a protective chain, and a complexone as a reporter group is provided. This synthetic composition is especially suitable as a macromolecular contrast agent.

Scheme 1

The compositions may be prepared in two stages by first reacting polyamino acid with activated MPEG analogs, and then reacting this reaction mixture with an activated chelating compound. This procedure is preferred when poly-l-lysine is used as the polymeric carrier (See FIG. 1).

ε-amino groups of poly-l-lysine were reacted with activated derivatives of carboxylated MPEG, e.g., acid chlorides, anhydrides, mixed anhydrides, nitrenes, isothiocyanates and imidazolides, and activated esters, e.g hydroxysuccinimide, hydroxysulfosuccinimide, p-nitrophenyl, benzotriazolide.

The chelating molecule is brought into reaction with the remaining amino groups, either in activated form, e.g., anhydride, mixed anhydride, or isothiocyanate, or in a non-activated form. If the chelating molecule is in the non-activated form, it is activated to obtain an activated ester in the presence of succinimide or sulfosuccinimide and carbodiimide and is then brought into reaction with the remaining amino groups. The reaction may be preceded with an additional chemical modification of the polyamino acid backbone or MPEG chains which are not limited to reactions resulting in the formation or elimination of at least one chemical bond.

The sequence of chemically linking the protective chains and a reporter group to a polymeric carrier may be reversed, i.e., linking of a reporter group preceeds linking of protective chain(s) to the polymeric carrier, but preferably, the reporter group is used as a monofunctional activated analog, i.e., one molecule of activated reporter group forms only one covalent linkage with a polymeric carrier.

Scheme 2

The compositions also may be synthesized using standard peptide synthesis protocols with modified amino acid precursors such as MPEG-amino acid and complexone-amino acid. In this case, moieties of complexone and PEG may be alternated in a controllable manner.

Scheme 3

Oligomers of PEG-polyamino acids may be conjugated with oligomers of complexone-amino acids to form a block-co-polymer.

All three schemes will result in predictable compositions with highly predictable molecular weight distributions.

When carboxylated carriers are used, such as carboxylated saccharides, or polyaminoacids with carboxy groups in their radicals, such as poly-l-aspartic acid, the polymeric carrier is preferably activated in the presence of carbodiimide and sulfosuccinimide, as described in Example 2 for DTPA, and then reacted with aminated protective chains, such as MPEG monoamine at pH 7–9. The linking of complexone or chelate is then achieved preferably by carbodiimide condensation.

When used for medical imaging, the compositions of this invention preferably have a non-proteinaceous polyamino acid molecule serving as a carrier of covalently attached activated analogs of linear or branched chelating molecules, to which a MR reporter cation is linked, i.e., ionically chelated. The carrier forms a single chemical entity with protective chains of MPEG.

The synthetic route of preparing the compositions of this invention includes covalent modification of the polyamino acid carrier. Conjugation of 1,1'-carbonyldiimidazole-treated MPEG to aminogroups requires high excesses of the modifier, e.g., activated MPEG, which leads to the formation of semi-stable gels since the solubility of polyamino acids in the presence of MPEG is reduced. The procedure for preparing N-hydroxysuccinimidyl MPEG-succinate described in Scheme 1 gives a product with a highly activated ester content, e.g., greater than 75%, which is advantageous for preparing the compositions of this invention. Special purification of intermediates enables elimination of peroxides and yields a preparation for in vivo use.

Linking MPEG to the polymeric carrier, e.g., polyamino acid, also prevents possible cross-linking of the poly-amino acid with the cyclic anhydride of DTPA. MPEG chains prevent the formation of by-products because they create a steric barrier for cross-linking the reagent. Therefore, the formation of high-molecular weight products can be controlled, which makes the synthetic steps predictable. As a result, a homogenous preparation is obtained with a narrow molecular weight distribution.

The polymeric carriers preferably contain peptide bonds. The same bonds are involved in conjugating a chelating molecule with reactive groups of the amino acid radicals. The compositions, therefore, are potentially biodegradable by various animal non-specific peptidases. To assist in vivo elimination of polymeric carrier and protective chains together with a reporter group, or to enhance dissociation of a reporter group from the carrier to the biological milieu if such a reporter group is a therapeutic agent, elements of polymeric carrier or protective chains or reporter groups could be linked together by a semistable linkage, such as S—S bonds. Small amounts of trapped compositions may be removed from the body by degradation to smaller fragments. However, a variety of activated PEG derivatives may be used for the preparation of the compositions thus making them either virtually undegradable or, on the contrary, labile. However, labile compositions are undesirable, since detaching MPEG will result in more extensive accumulation of the contrast agent compositions in the reticuloendothelial system.

The use of the compositions of this invention in MR imaging requires the presence of an MR reporter group, such as a paramagnetic cation, e.g., gadolinium (III). The transchelation technique developed for this experiment is based on an embodiment of Harris et al., *J. Polym. Sci.*, 22:341–52, which is incorporated herein by reference. Applicants used Gd-citrate to prevent the contact of the contrast agent with gadolinium oxides, used previously by Griess et al., U.S. Pat. No. 4,647,447, or gadolinium chloride, used previously by Bardy et al. U.S. Pat. No. 4,804,529. The gadolinium citrate easily forms contaminants such as colloidal hydroxides at pH values greater than 6.5, which is within the range of optimal pH values for the NMR contrast agents of this invention. The addition of a special purification step, e.g., an anion-exchange chromatography step, allows the separation of Gd-labeled MPEG-PL-DTPA (Gd) from possible anionic contaminants, e.g., MPEG-PL-DTPA(Gd) with a low degree of substitution of amino groups with MPEG or small amounts of PL-DTPA(Gd).

The protective chains, e.g., MPEG, of this invention do not react with the C3 component of complement which is a distinct advantage over previously known agents, e.g. dextran-DTPA(Gd), which are known to react with the C3 component of complement.

MPEG prevents the exposure of chelating groups and paramagnetic cations to receptor cells, e.g., glomerulonephral phagocytes, capable of recognizing them. MPEG also forms a steric barrier which prevents rechelation of Gd cations by serum proteins such as transferrin. The compositions of this invention also prevent possible delayed toxic effects of re-chelated gadolinium.

MPEG conjugation lowers the toxicity of the composition of this invention by preventing significant accumulation of the chelating polymer in the liver and spleen. Acute toxicity studies of the compositions of this invention have indicated no apparent toxicity in mice at concentrations exceeding 10–35 times the optimal doses. Histological examination of tissues of these mice have shown no deviations from control animals.

Figure 2:
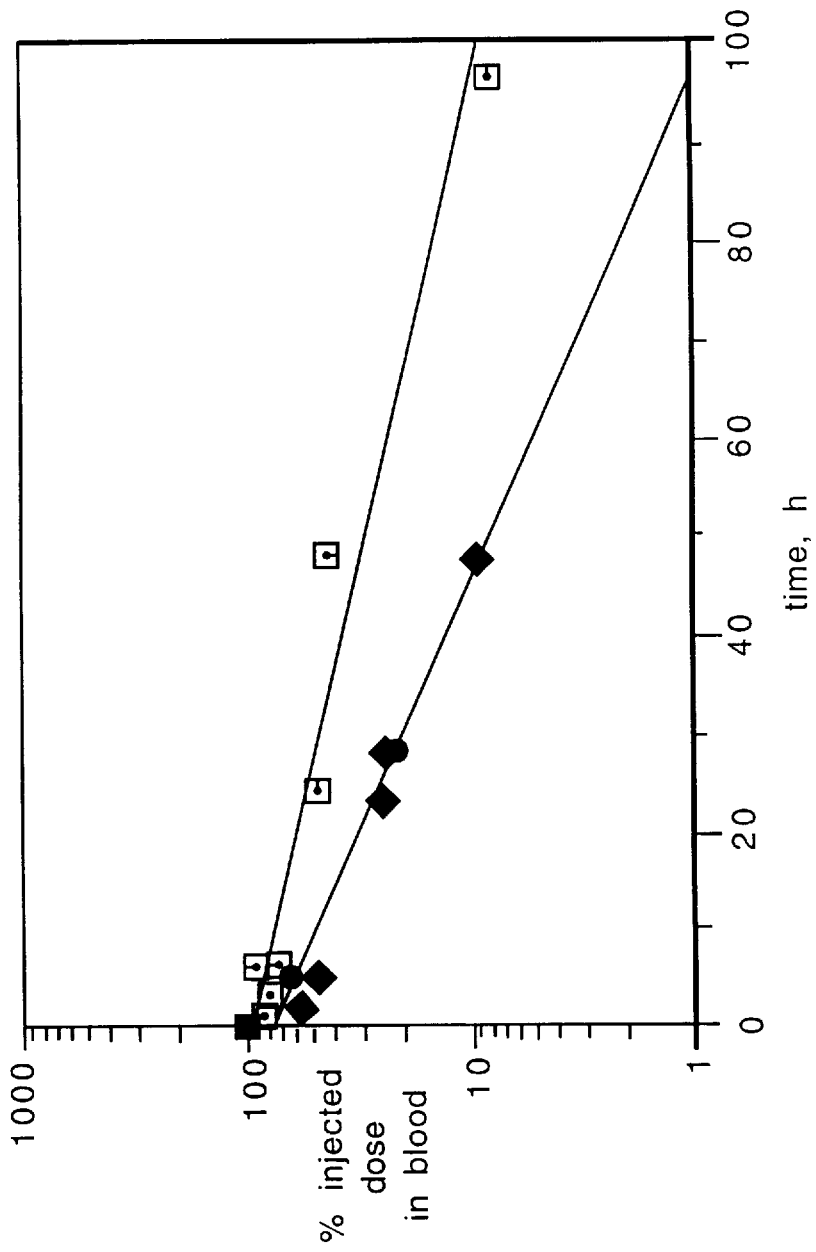
FIG. 2 is a graph of the blood clearance of [$^{111}$In]-labeled and Gd-saturated MPEG(MW 5 kD)-poly-l-lysine(MW 53.5 kD)-DTPA (squares) and MPEG(MW 2 kD)-poly-l-lysine (MW 41 kD)-DTPA (diamonds).

The blood half-life of the compositions of the invention was determined in rats. The radioactive and paramagnetic contrast agents were incorporated into the composition prepared according to Examples 1 and 3 in order to accurately determine its pharmacokinetic characteristics in vivo. The rats were visualized at different time points using a gamma camera to follow the distribution of the composition. As indicated by the data presented in FIG. 2, the blood half-life of the disclosed contrast agent was equal to 24 hours for MPEG(MW 5 kD)-poly-l-lysine(MW 53.5 kD)-DTPA labelled with [$^{111}$In] and saturated with gadolinium, while a smaller contrast agent MPEG(MW 2 kD)-poly-l-lysine(MW 25 kD)-DTPA labelled with [$^{111}$In] and saturated with gadolinium, was removed from the blood at a faster rate with the t½ being 6 hours. The only two sites in the body where accumulation of these compositions was detected in quantities significantly larger than 1% of injected dose per gram of tissue, were the spleen and kidneys. However, the total amount of contrast agent entrapped in both kidneys and spleen did not exceed about 7% of the contrast agent in the composition.

Figure 3:
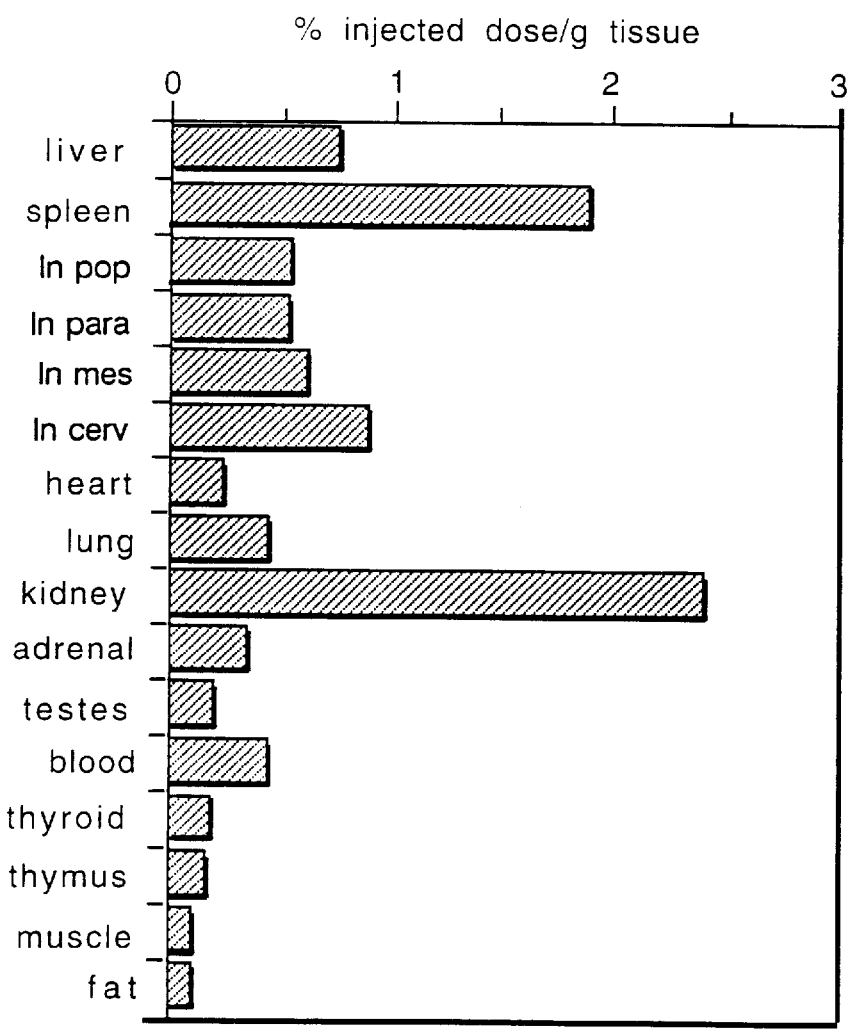
FIG. 3 is a graph of the biodistribution of [$^{111}$In]-labelled and Gd-saturated MPEG(MW 5 kD)-poly-l-lysine(MW 53.5 kD)-DTPA 90 hours after intravenous injection.

The typical biodistribution 90 hours post-injection of MPEG(MW 5 kD)-poly-l-lysine(MW 53.5 kD)DTPA, labelled with [$^{111}$In] and saturated with gadolinium is presented in FIG. 3. The total amount of the composition retained in the liver, spleen and both kidneys totaled 15–18% after 90 hours in circulation. The above data indicates that the contrast agents of this invention do not accumulate in the reticuloendothelial system of animals after intravenous injection in significant amounts and may be removed from circulation, presumably by degradation in the blood, through bile excretion, and by kidney filtration.

Immunogenicity

Prevention of the interaction of the reporter group with plasma proteins by MPEG chains hinders the binding of the compositions with cells capable of opsonin recognition, e.g., antigen presenting phagocytes, and with immunocompetent blood cells, e.g., resting B-cells. As a result, the formation of an immune response to the reporter group itself is unlikely and the production of host antibodies to the reporter group is largely avoided. This enables the repetitious use of the composition of this invention if necessary. The immune response of animals to intravenous injections of the compositions of this invention have detected no antibody formation to PEG and acetylated polyamino acid.

Figure 4:
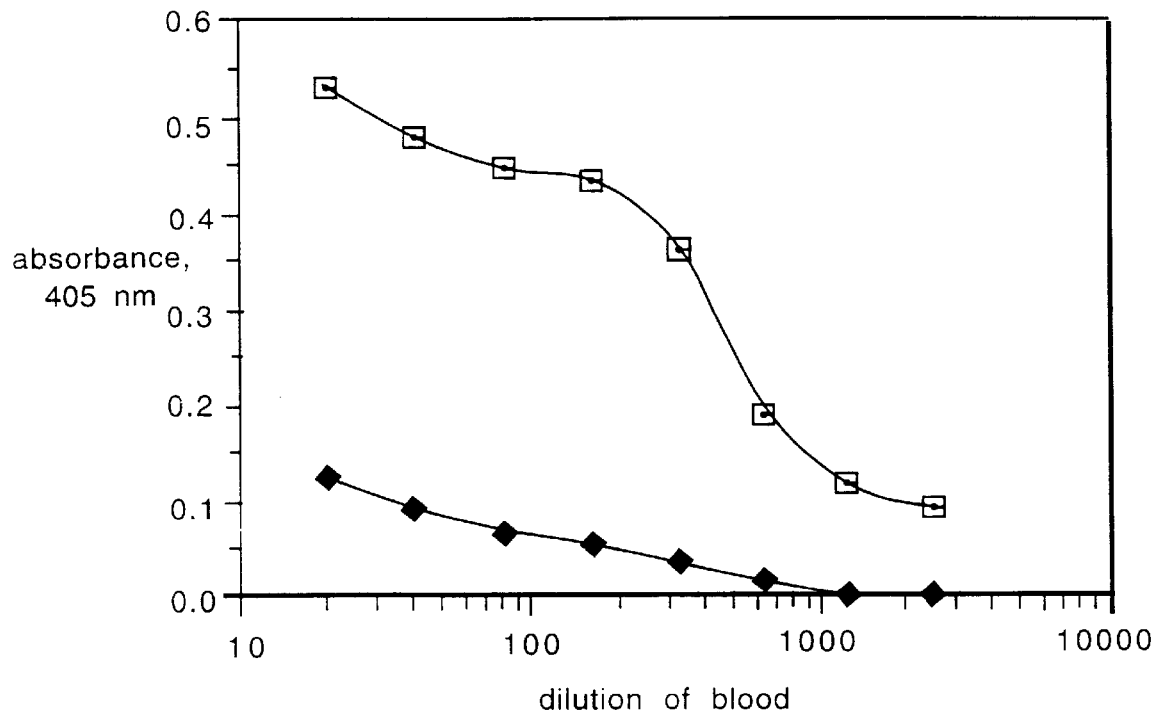
FIG. 4 is a graph of the response to Gd-DTPA of mice injected with Gd-DTPA-BSA (squares) and MPEG(MW 5 kD)-poly-l-lysine (MW 53.5 kD)-DTPA(Gd) (diamonds).

Applicants detected the formation of low-avidity, e.g., titer of 800–1,000, of antibodies to DTPA(Gd) in animals injected with BSA-DTPA(Gd) by enzyme-linked immunoadsorbent assay (ELISA), and demonstrated virtually no response in animals injected with compositions of this invention (See FIG. 4). Substantially, no detectable antibodies against DTPA(Gd), acylated polylysine or MPEG were found in animals injected intravenously or intraperitoneally with compositions of this invention 20 days post-injection.

The combination of long-blood half-life and lack of immunogenicity is an important feature of this invention.

Figure 5:
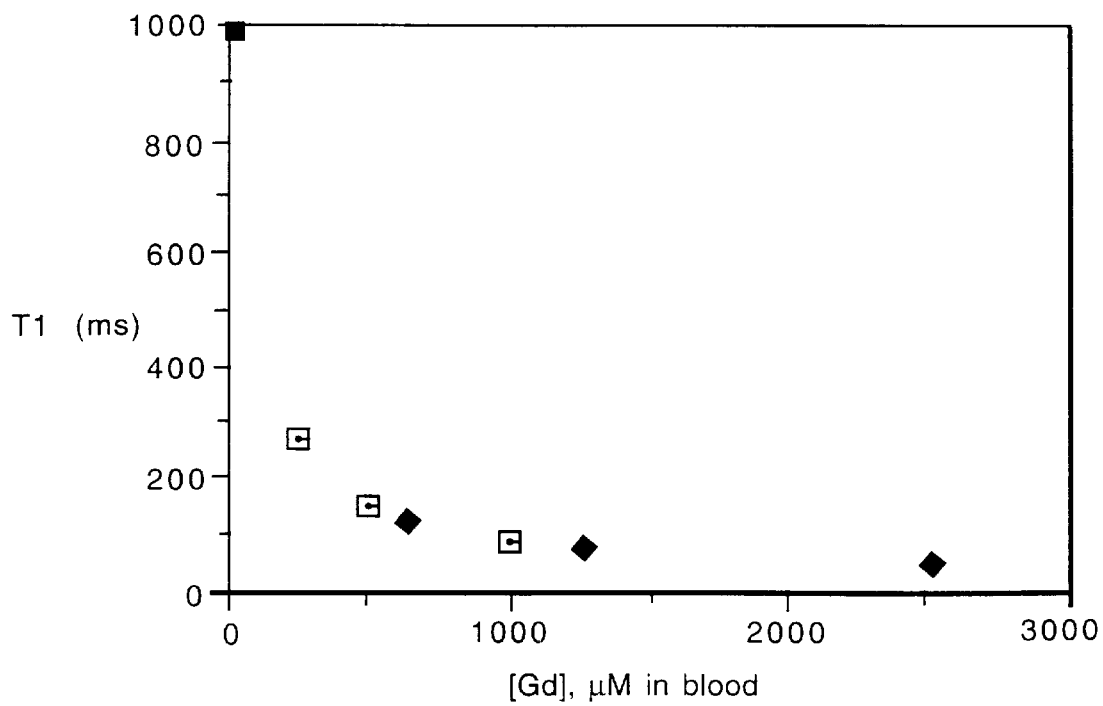
FIG. 5 is a graph of the effect of Gd-labelled MPEG(MW 2 kD)-poly-l-lysine(MW 41 kD)-DTPA (squares) or Gd-labelled MPEG(MW 5 kD)-poly-l-lysine(MW 25 kD)-DTPA (diamonds) on T1 values of blood at various concentrations.

The compositions of this invention have demonstrated a surprisingly high capacity, e.g., up to 13% by weight, for gadolinium and exceptionally high R1/Gd atom, e.g., 20 mM-1 sec-1. Preliminary experiments showed that high-quality angiograms could be obtained when T1 values of blood are decreased at least 5-fold as a result of the injection of the contrast agent. As determined by measuring T1 values in blood, the Gd concentration which allows a 5-fold decrease in T1 corresponds to ca. 300 nmol. Gd/ml of blood (See FIG. 5). In a typical human study this corresponds to an injection of ca. 20 μmol Gd/kg of total body weight, which is 5-fold lower than for Gd-DTPA dimeglumine, which is a frequently used MR contrast agent.

Figure 6:
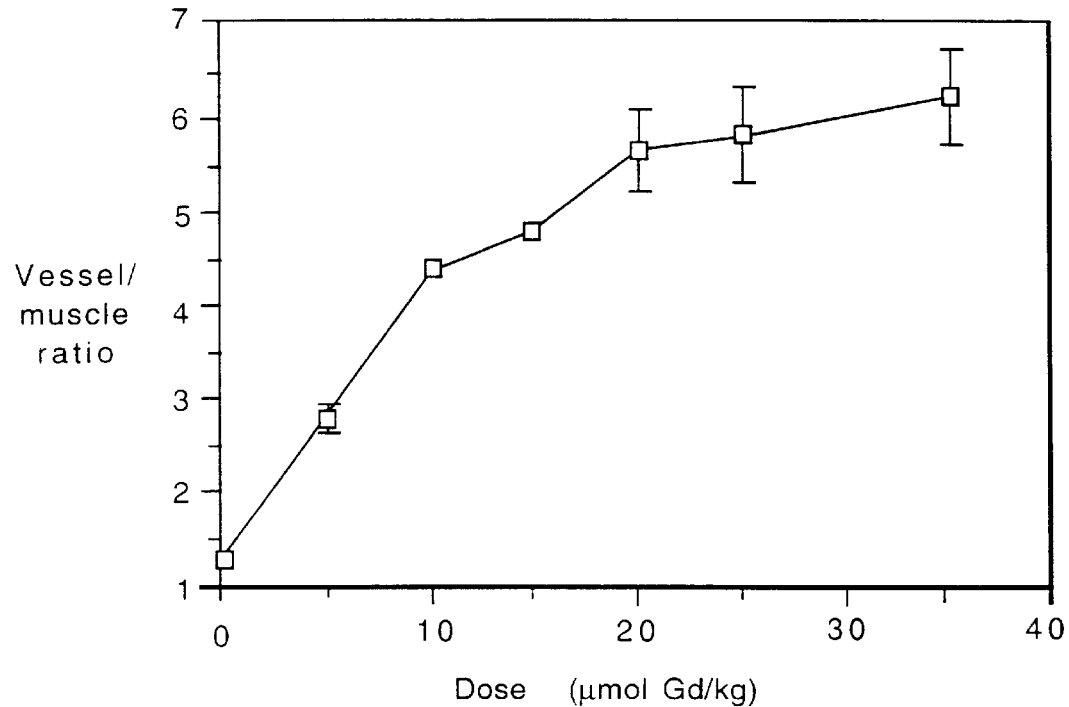
FIG. 6 is a graph of the dose-dependent enhancement of vessels, with the vessel/muscle ratio determined by digitization of signal intensities of several large arteries, e.g., aorta, iliac, and femoral, and nearby muscle tissue.
Figure 7:
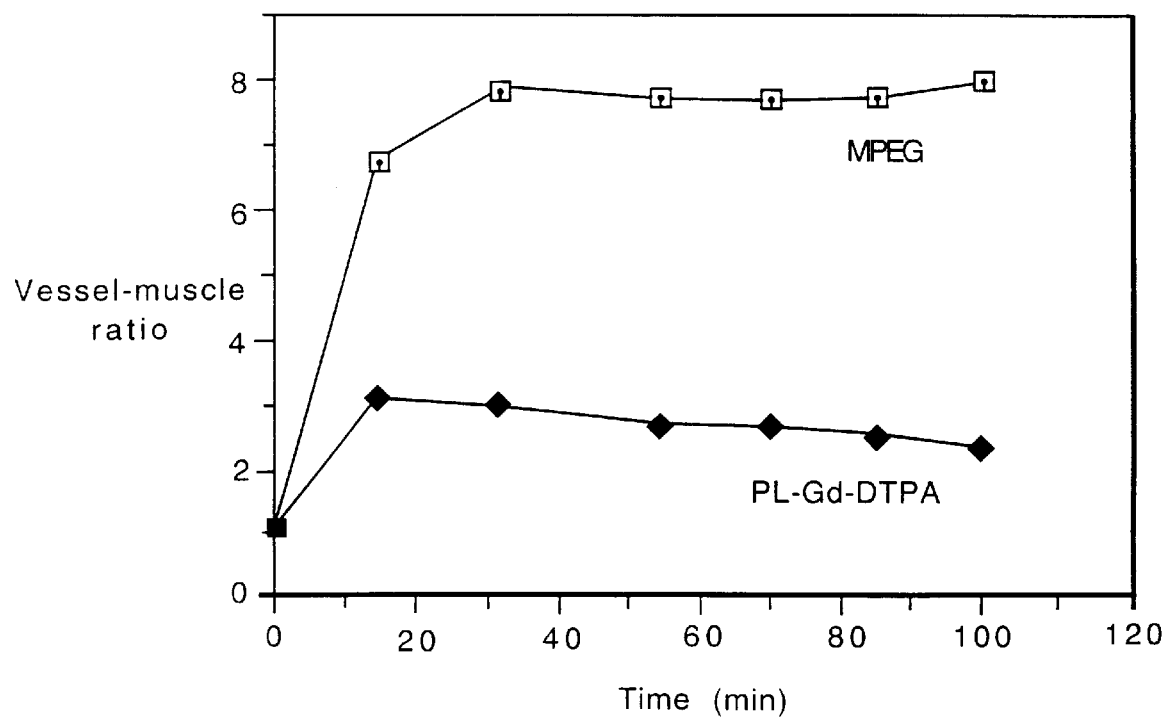
FIG. 7 is a graph of the time-course of a contrast agent in large vessels in a comparative study.

Dose dependence of vessel/muscle signal ratio reveals a plateau at the saturation dose of 20 μmoles of Gd/kg of total body weight (See FIG. 6). At this concentration a contrasted vessel image had a vessel/muscle ratio of 5.5–6, which is a 4-fold increase over previously known preparations administered at a concentration of 50 μmoles Gd/kg total body weight. The compositions of this invention were far superior, i.e., greater than 200%, to poly-l-lysine (MW 25 kD)-DTPA(Gd) in increasing the blood/muscle ratio (See FIG. 7). In this comparative study, rats were injected with 20 μmoles Gd/kg of MPEG(MW 5 kD)-poly-l-lysine(MW 25 kD)-DTPA(Gd) (MPEG squares) or with 50 μmoles Gd/kg of polylysine(MW 25 kD)-DTPA(Gd) (PL-Gd-DTPA, diamonds (See FIG. 7). The increase in vessel/muscle ratio leveled out within 30 minutes and remained constant for the time of observation, which was 100 minutes. Because MPEG(MW 5 kD)-poly-l-lysine(MW 25 kD)-DTPA(Gd) had a higher vessel/muscle ratio, the images of vascular anatomy were considerably better after administering compositions of the invention than after administration of PL-Gd-DTPA.

Figure 8A:
FIGS. 8a and 8b are MR images of the head of a rat in 3-D bright-pixel reconstruction showing the image before (FIG. 8a) and after (FIG. 8b) an intravenous injection of MPEG (MW 5 kD)-poly-l-lysine(MW 25 kD)-DTPA(Gd).
Figure 8B:
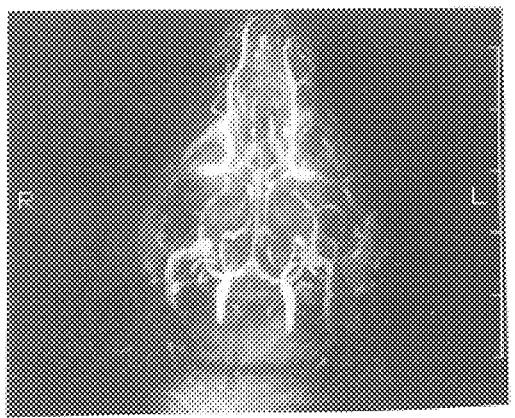

This enabled a dramatic decrease of the dose of Gd required to produce high-quality angiographic images in rats (See FIGS. 8a and 8b). In one study, the MR images of the head of a cat were compared before (See FIG. 8a) and after (See FIG. 8b) intravenously injecting MPEG(MW 5 kD)-poly-l-lysine(MW 25 kD)-DTPA (Gd) at 30 μmol Gd/ml. The images were taken 20 minutes after injection on a Signa (GE Instruments, 1.5 T, 3-TOF SPGR/90 SE 60/6.5 256×192 2 NEX) using a 3 inch surface coil. The 3-D bright-pixel reconstructions of vessel maps provided a very high vessel/background signal ratio, eliminating the need for background subtraction. Contrary to known constrast agents, the compositions of the invention injected at 30 μmoles Gd/kg total body weight surprisingly resulted in resolution of submillimeter vessels having an internal diameter of less than 1 mm.

Figure 9:
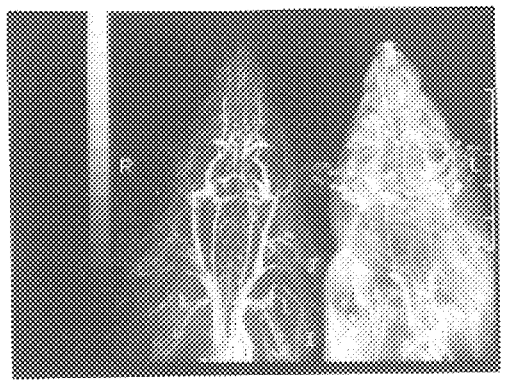
FIG. 9 is an MR image of two rats in 3-D bright-pixel reconstruction after an intravenous injection of MPEG(MW 5kD)-poly-l-lysine(MW 25 kD)-DTPA(Gd) (left image) and gadopentate dimeglumine (right image).

A comparative study between MPEG(MW 5 kD)-poly-l-lysine(MW 25 kD)-DTPA(Gd) and gadopentate dimeglumine indicated significantly better results for PEG-poly-l-lysine(MW 25 kD)-DTPA(Gd). In one study, one rat was intravenously injected with MPEG-poly-l-lysine-DTPA(Gd) (20 μmol Gd/Kg total body weight) (left image) and one rat was intravenously injected with gadopentate dimeglumine (100 μmol Gd/kg, from Magnevist®, Berlex Labs) (right image). Immediately, i.e., 10 minutes, following the intravenous administration of Gd-DTPA or the MPEG derivative, the vessel/muscle ratios had increased from 1.4 to 2.7, and 1.4 to 4.5, respectively. Thirty minutes after administration, the ratios were 2.0 for Gd-DTPA and 5.8 for the MPEG(MW 5kD)-poly-l-lysine(MW 25 kD)-DTPA(Gd) at a p-value less than 0.001 (See FIG. 9). Gd-DTPA initially yielded a small increase in vessel contrast. However, as Gd-DTPA is distributed through the extravascular space, contrast is lost. The MPEG derivative compositions of the invention, because of their unique vascular distribution, consistently resulted in high ratios. The images were taken on a Signa using a 5 inch surface coil (See FIG. 9).

Figure 10A:
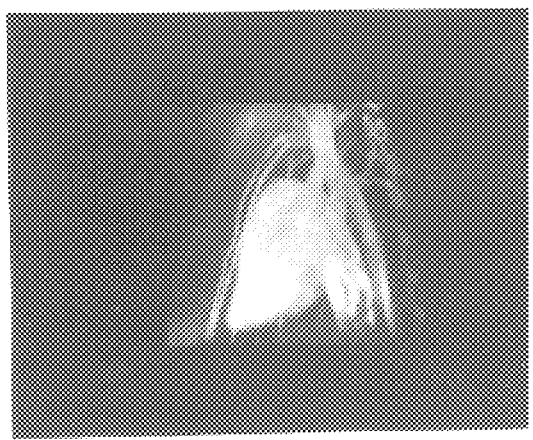
FIGS. 10a and 10b are of MR images of a rabbit in 3-D bright-pixel reconstruction of the lateral (FIG. 10a) and cranio caudal projection (See FIG. 10b) after an intravenous injection of MPEG (MW 5 kD)-poly-l-lysine(MW 25 kD)-DTPA(Gd).
Figure 10B:

Imaging experiments with rabbit and minipig (body weight 40 kg) thorax were performed demonstrating the feasibility of visualizing the pulmonary and coronary arteries using the compositions of this invention (See FIGS. 10a and 10b). In one study, a rabbit was intravenously injected with MPEG(MW 2 kD)-poly-l-lysine(MW 41 kD)-DTPA (Gd) (20 μmol Gd/ml). The images were taken 20 minutes after injection on a Signa using a 5 inch surface coil.

Figure 11A:
FIGS. 11a and 11b are MR images of the left flank and thigh of a rat in 3-D bright-pixel reconstruction before (FIG. 11a) and after (FIG. 11b) an intravenous injection of MPEG (MW 5 kD)-poly-l-lysine(MW 25 kD)-DTPA(Gd). Images were taken two weeks after injection of R3230 mammary adenocarcinoma cells into the left flank of the rat.
Figure 11B:
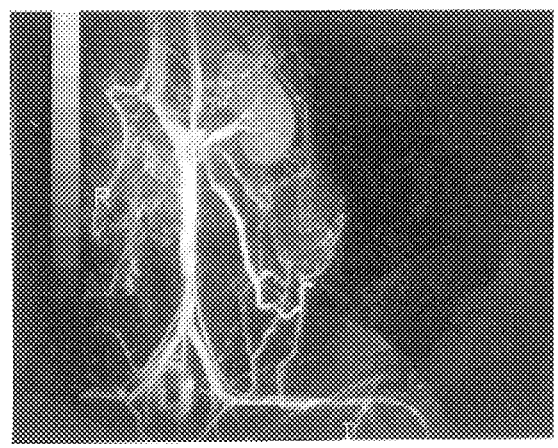

The utility of the compositions of this invention to reveal abnormalities of vessels in experimentally induced pathological conditions was tested in rabbits and rats. By 3-D TOF (Time of Flight) MR angiography the narrowing of the femoral artery at the site of experimental stenosis could be reliably visualized. For visualization of vessel abnormalities in tumor progression, rats with R3230 mammary adeno carcinoma were used. In one study, the MR images of the left flank and thigh of a rat are shown before (See FIG. 11a) and 20 minutes after (See FIG. 11b) an intravenous injection of MPEG (MW 5 kD)-poly-l-lysine(MW 25 kD)-DTPA (Gd) at 20 µmol Gd/ml. The images were taken on a Signa (GE Instruments, 1.5 T, 3-TOF SPGR/60 SE 60/6.5 256×192 2 NEX) using a 3 inch surface coil.

Experiments with neoplasia in rats using 20 µmol Gd/kg provided exclusively informative contrast-enhanced angiograms. The location, size, and borders of the tumor and descending veins could be easily recognized on collapsed 3-D MR images. Therefore, the compositions of this invention may be used for detection of both neoplasia and tumor neovascularity which is important in clinical practice for staging and surgical planning.

Additional animal studies using the compositions of the invention were performed to investigate in vivo gamma imaging; biokinetics; immune response; and magnetic resonance imaging.

In vivo gamma-camera imaging

Sprague-Dawley rats (200–250 g) were injected into tail vein using a 26 gauge needle with 1–10 mg/0.5 ml of product I or III, labeled with [$^{111}$In] and Gd, as described in Example 6. Images on a gamma-camera (from Ohio Nuclear) using parallel medium-energy collimator were obtained 30, 60, 120 minutes, and 24 and 70 hours after injection.

Biokinetics of the contrast agent

The Biokinetics of Gd-and [$^{111}$In] labeled product (III or I) was studied using Sprague-Dawley rats ranging from 230–250 g. The animals were injected in the tail vein with 1–10 mg of polymer (60–70 µCi/kg, 2 µm/kg Gd) using a 26 gauge needle under ether anesthesia. Little variation in kinetics was detected within these dose limits. The biodistribution of labeled product was determined in 16 organs, i.e., organ tissues, by measuring radioactivity at each time point indicated on graphs. Two rats were used for each point (See FIG. 3).

Testing of immune response in mice

A 0.2 ml sample of product I (0.5 mmol Gd/kg, i.e. 20-fold imaging dose) was injected intravenously or intraperitoneally into $C_3H$/He mice (n=2). Control animals received BSA-DTPA(Gd) with equal amount of Gd-DTPA, prepared as described in Hnatowich D. J. et al. Science 1979, in the same volume of saline. Animals were observed for 2 weeks for signs of toxicity. No signs of toxicity were detected. After the 2 week period, blood was collected from the tail vein of animals and titer of antibodies was detected by enzyme-linked immunoadsorbent assay (ELISA). ELISA plates were coated with ovalbumin-DTPA(Gd), ovalbumin-MPEG, BSA or acetylated poly-l-lysine (MW 70,000). Only wells of the plate coated with ovalbumin-DTPA(Gd) showed specific binding of mouse immunoglobulins.

MR Imaging

To visualize blood vessels in experimental animals, 0.005–0.05 mmol Gd/kg of product II was injected in male Sprague-Dawley rats (260–360 g) using a 26 gauge butterfly needle in 0.3 ml of sterile saline under barbiturate-induced anesthesia. Appropriate surface coils, 5 inch for two animals and 3 inch for one animal, were applied (See FIGS. 8a and 8b, and FIG. 9).

In experiments with rabbits and minipigs, animals were intubated. Anesthesia was performed with the use of an inhalant Isoflurane. Electrocardiography was constantly monitored. Product II was injected at 0.03 mmol Gd/kg via catheter inserted in the left femoral artery. An extremity surface coil was used for the rabbit studies; a head coil was applied in the minipig studies (See FIGS. 10a and 10b).

In rat studies, 48 saggital slices were imaged on General Electric CSI (thickness=0.7 mm) using a T1-weighted 3D—Time of Flight SPGR pulse sequence (1.5 T, SE 50/6.5, flip angle 60). In rabbit and minipig studies up to 80 slices were imaged (See FIGS. 10a and 10b).

Use of the Compositions as Contrast Agents

The compositions of this invention may be used in medical imaging, and administered intravascularly or by bolus-injection. The vascular images are enhanced due to changes of blood relaxivity or radioactivity. The contrast agents may be used for the improvement of vascular images of large vessels, e.g., arteries and veins, or to visualize small vessels, e.g., submillimeter capillaries. The resolution of the images is increased by providing more detailed information. The contrast agents may be used for vascular anatomy mapping, determination of vessel stenosis, abnormal vascularity, e.g., neovascularity, normal perfusion, perfusion defects, or functional imaging of the brain.

Use of the Composition as a Therapeutic Agent

The compositions of this invention may also comprise a therapeutic agent, e.g., one or more species of cytostatics, analgesics, antiinflammatory, antiviral, antifungal or psychotropic drugs. The compositions of this invention which include therapeutic agents are beneficial because the prolonged circulation of the composition in the blood substantially prolongs the therapeutic effect of the therapeutic agent. To achieve a therapeutic effect the therapeutic agent should slowly detach or leave the polymeric carrier. This may be achieved by detachably linking or positioning a semipermeable membrane around the carrier to form a vesicle, allowing the drug concentrated in the vicinity of polymeric carrier to slowly diffuse through the membrane into the intravascular space. The compositions of this invention which include therapeutic agents may be administered intravascularly or by bolus-injection.

The compositions of this invention are described in the following Examples and Experimental section which form embodiments of the present invention and should not be regarded as limiting the scope of invention.

EXAMPLES AND EXPERIMENTAL RESULTS

Example 1

Synthesis of PEG-poly-l-lysine (300)-DTPA, Product I

Synthesis of MPEG succinate

Dissolve 6.5 g of MPEG (MW 2000) in 25 ml of peroxide-free dioxane at 60° C. and mix with preheated solution of 1.6 g of succinic anhydride at a 5-fold molar excess in 25 ml of dioxane Dissolve 300 mg of N,N'-dimethylaminopyridine as a catalyst in 10 ml of dioxane and add to the reaction mixture. Incubate the mixture to at 90° C. for 5 hours. Remove the dioxane by rotary evaporation at 40° C., and dissolve the solid in a minimal amount, e.g., 7–10 ml, of methylene chloride, cool to −10° C. and filter on a fritted-glass filter to remove the precipitate of succinic acid. Add 300 ml of ethyl ether per each 5 ml of filtrate and maintain the cloudy solution at −20° C. to precipitate MPEG succinate. Filter the precipitate on a fritted glass filter and wash with ethyl ether.

Dissolve 5.6 g of the dry precipitate with 40 ml of water and pass through an AG 50W X8 resin, (15 g of wet resin, treated with 50% ethanol and deionized water) on a 30-micron fritted glass filter in order to remove the remaining catalyst.

A 5 g sample of MPEG2000 succinate was obtained (86% yield) as a white amorphous solid. The Rf was 0.8 on silica gel 60 TLC plates (from EM Sciences) (developed by a solution of chloroform:methanol:15 mM CaCl2 in a ratio of 65:35:2). The Rf was 0.5 on RP-18 TLC plates (from EM Sciences) in the same system after staining with iodine vapor.

Synthesis of MPEG succinyl-N-hydroxysuccinimidyl ester

Dissolve the lyophilized MPEG succinate product (2 g, 0.5 mmol) in 10 ml of peroxide-free dioxane, which passed the peroxide-sensitivity test. Sequentially add 0.11 g N-hydroxysuccinimide (Fluka Chemie AG, Buchs, Switzerland) and 0.15 g (0.55 mmol, 1.1 molar excess) of dicyclohexylcarbodiimide (Fluka Chemie AG, Buchs, Switzerland) to the mixture. Stir the reaction mixture for 6 hours at room temperature and cool on ice. Remove dicyclohexylurea by filtration through fritted glass filter or through a GF-C glass wool filter. Remove dioxane on a rotary evaporator, and add 10 ml of methylene chloride and mix with 100 ml of ether under continuous stirring. Store the precipitate at $-20°$ C. overnight. Separate the product by filtration and recrystallize from a dichloroethane:ether mixture at a ratio of 1:9.

Test for an activated ester of MPEG succinate

The percent of the activated ester in solid was determined by solubilizing 1.5 mg of product in anhydrous DMSO (100 $\mu$l). Add 10 $\mu$l of the solution to 800 $\mu$l of 0.05M sodium phosphate (pH 8.5). Record the absorbance at 260 nm for 30 minutes. An increase in absorbance was due to hydrolysis of activated ester (e260=8260 [mol cm]-1 for N-hydroxysuccinimide at pH 8.5). Approximately 75% of the composition obtained was found to be an activated ester. The Rf was 0.95 on the silica gel 60 (developed by a solution of chloroform:methanol:15 mM CaCl2 at a ratio of 65:35:2) after UV visualization with ammonia fumes.

Synthesis of MPEG-poly-l-lysine-DTPA.

Dissolve 816 mg of poly-l-lysine (PL hydrobromide, MW 67,700 (Sigma Chemical Co), DP: 324 l-lysine residues, 25 mM epsilon-aminogroups of l-lysine, hydrobromide) in 38 ml of 0.1M carbonate buffer (pH 8.7). Dissolve 3.1 g MPEG succinyl hydroxysuccimidyl ester (MPEGOSu, MW 2,200) in 15 ml of dry DMSO. Add the MPEGOSu solution drop-wise to the PL solution with agitation and incubate the mixture for 2 hours under stirring.

The degree of modification was checked by trinitrobenzenesulfonic acid titration, as used in Spadaro, A.C.C. et al., Anal. Biochem. 96:317 (1979). Mix 10 $\mu$l of the sample, 100 $\mu$l of water, 100 $\mu$l of 10% Triton X-100, 100 $\mu$l of 0.1M of sodium tetraborate, and 0.35 ml of 2 mg/ml of TNBS in a tube. Incubate for 45 minutes. Stop incubation by addition of 2.3 mg/ml sodium sulfite in 5M $NaH_2PO_4$. The absorbance was determined at 420 nm and compared with that of PL. The amount of modified groups was determined to be equal to 30%.

A suspension of a cyclic anhydride of DTPA (0.5 g/ml in DMSO) was prepared by adding 200 $\mu$l portions (1.5 g of cDTPA total) to the solution of PL and MPEG, and the pH was adjusted to 8 with 5N NaOH after each addition. The amount of titratable aminogroups was checked again and no free aminogroups were detected.

Purification of MPEG-poly-l-lysine-DTPA

Dilute the reaction mixture of MPEG-poly-l-lysine-DTPA (MPEG-PL-DTPA) to 300 ml with 0.2M sodium citrate (pH 6.), filter through 0.45 $\mu$ nylon filter and dialyze in a flow-through cell using a membrane with cut-off of 100 kD (for globular proteins). Concentrate to 30–50 ml and dilute to 300 ml with citrate. Repeat the procedure 2 times using water instead of citrate in the last stage. Concentrate the solution to 15 ml, and lyophilize. Alternatively, the sample may be filtered through sterile 0.2 $\mu$m membrane and stored at 4° C. A table of the theoretical and actual chemical analysis is presented below:

Chemical analysis: Theoretical % C 46.7, % H 7.0, % N 8.0 Actual % C 41.2, % H 6.4, % N 9.7

Example 2

Synthesis of MPEG(MW 5 kD)-poly-l-lysine (MW 25 kD)-DTPA, Product II

Synthesis of MPEG succinate

Dissolve 40 g of MPEG (MW 5000) in 250 ml of peroxide-free dioxane at 60° C. and mix with a preheated solution of 8 g of succinic anhydride (10-fold molar excess) in 50 ml of dioxane. Dissolve 900 mg of N,N'-dimethylaminopyridine as a catalyst in 10 ml of dioxane and add to the reaction mixture. Incubate the mixture at 90° C. for 8 hours.

Remove the dioxane by rotary evaporation at 40° C., and dissolve the solid in 20 ml of methylene chloride, cool to $-10°$ C., and filter on a fritted-glass filter to remove the precipitate of succinic acid. Add 300 ml of ethyl ether per each 10 ml of filtrate and precipitate the cloudy solution of MPEG at $-20°$ C. succinate. Filter the precipitate on a fritted glass filter (10–20 $\mu$, Corning) and wash with cold ethyl ether.

Dilute 35 g of the dry precipitate with 100 ml of water and pass through AG 50W X8 resin (25 g of wet resin, treated with 50% ethanol and deionized water) on a 100-micron glass filter in order to remove the remaining catalyst. In order to reduce the amount contaminating peroxides, treat the solution of MPEG2000 succinate in water with 10 mM sodium borohydride for 4 hours at room temperature. Lyophilize the solution, redissolve the solution in methylene chloride (0.1 g/ml), and resediment the solution with the addition of diethyl ether. A 30 g sample of MPEG5000 succinate sample was obtained (an 83% yield) as white amorphous solid. The Rf was 0.5 on RP-18 TLC plates (from EM Sciences) (developed in a solution of chloroform:ethanol:water at a ratio of 65:25:4) after staining with iodine vapor.

Synthesis of MPEG succinyl-N-hydroxysuccinimidyl ester

Dissolve 5.29 g (1 mmol) of the lyophilized MPEG succinate product in 40 ml of peroxide-free tetrahydrofurane, which passed peroxide-sensitive test, and add 0.17 g N-hydroxysuccinimide (1.5 mmol, Fluka Chemie AG, Buchs, Switzerland) and 0.3 g (1.1 mmol) of dicyclohexylcarbodiimide (Fluka). Stir the reaction mixture for 6 hours at room temperature and then cool on ice. Remove the dicyclohexylurea by filtration through a fritted glass filter (20–30 $\mu$, Corning). Remove the tetrahydrofurane on a rotary evaporator, add 10 ml of methylene chloride and mix with 100 ml of ether under continuous stirring. Precipitate at $-20°$ C. overnight. Separate the product by filtration and recrystallize from a dichloroethane:ether mixture at a ratio of 1:9.

Test for an activated ester of MPEG succinate

The percent of the activated ester in solid obtained was determined as described in Example 1.

Synthesis of PEG-poly-l-lysine-DTPA

Dissolve 620 mg of poly-l-lysine (PL hydrobromide, MW 41,100, (Sigma Chemical Co.) DP: 196 l-lysine residues, 25 mM epsilon-aminogroups of l-lysine, hydrobromide) in 112 ml of 0.1M carbonate buffer (pH 8.7). Dissolve 2.9 g methoxy polyethylene glycolsuccinyl hydroxysuccinimidyl ester (MPEGOSu, MW 5,200) in 5 ml of dry DMSO. Add the PEGOSu solution drop-wise to the PL solution under agitation and incubate the mixture for 2 hours under stirring. Check the degree of modification by trinitrobenzenesulfonic acid titration as described in Example 1.

Prepare a suspension of cyclic anhydride of DTPA (0.5 g/ml in DMSO) by adding 200 µl portions (1.5 g of cDTPA total) to the solution of MPEG-PL and adjust the pH to 8 with 5N NaOH after each addition. Alternatively, the solution may be prepared by mixing of 2.5 mmol of DTPA, 0.5 mmol N-hydroxysulfosuccinimide (pH 4) and 0.5 mmol ethyl diaminopropylcarbodiimide in 50 ml of water. The solution is then mixed for 3 min and added to the mixture the solution of MPEG-PL (pH 8) Check the amount of titratable aminogroups. (No titratable amino groups were detected).

Purification of MPEG-PL-DTPA

Dilute the reaction mixture to 300 ml with 0.2M sodium citrate (pH 6), filter through 0.45 µ nylon filter, and dialyze in a flow-through cell using a membrane with a cut-off of 50 kD (for globular proteins). Concentrate to 30–50 ml and dilute to 300 ml with citrate. Repeat the procedure 2 times using water instead of citrate at the last stage. Concentrate the solution to 15 ml, and lyophilize. Alternatively, filter the sample through a sterile 0.2 µm membrane and store at 4° C. A table of the theoretical and actual chemical analysis is presented below:

Chemical analysis Theoretical % C 51.2, % H 8.2, % N 2.7 Actual % C 46.4, % H 7.8, % N 3.7

Example 3

Synthesis of MPEG-poly-l-lysine(MW 67 kD)-DTPA, Product III

Prepare according to the procedures of Example 1, using poly-l-lysine with a mean MW of 110,000.

Example 4

Synthesis of MPEG-poly-l-lysine (MW 53.5 kD)-DTPA, Product IV

Prepare according to the procedures Examples 1 and 2, using poly-l-lysine with a mean MW of 87,400 and MPEG (MW 5000)succinyl succinate.

Example 5

Synthesis of MPEG-poly-l-lysine(69)-(dithio) propionylpoly-l-lysine-DTPA, Product V Dissolve 50 mg of N-ε-benzoyloxycarbonyl-poly-l-lysine in 3 ml of dimethylformamide and treat with 10 mg of N-succinimidyl 3-(2-pyridyldithio)propionate in the presence of 20 µl of triethylamine. Incubate the product overnight and precipitate by the addition of 20 ml of water. Freeze-dry the precipitated product and divide into two equal parts. Redissolve the first part in dimethylformamide (0.5 ml) and treat for 20 minutes with 10 mM beta-mercaptoethanol, and precipitate by adding 10 ml of nitrogen-saturated water and freeze-dry. Redissolve this product together with the second part of the compound in 2 ml of dimethylformamide and add 5 µl triethylamine. Stir the mixture at room temperature overnight. Precipitate the product and wash with water, then redissolve the product in 1 ml of an HBr in glacial acetic acid solution, incubate for 1 hour, and mix with 20 ml of distilled ethyl ether. Wash the precipitate with ether and convert into MPEG-derivative and then into MPEG-DTPA derivative as described in Example 1, using DMFA instead of DMSO for solubilization of MPEG-succinyl succinate and DTPA cyclic anhydride.

Example 6

Preparation of [$^{111}$In]-Labeled Products I, II, III or IV

Prepare 100–500 µl of [$^{111}$In] citrate solution (pH 4.5) with total activity of 30–500 µCi. Dissolve 1 mg of products I, II, III or IV as prepared above in Citrate Balance Saline (CBS) of 10 mM citrate, 0.15M NaCl (pH 6.6). Mix the solutions and incubate for 30 minutes at room temperature. Purify by dialysis against 4 changes of 100 ml of the CBS. The dialyzed product was found to incorporate 98–100% of the radioactivity.

Example 7

Preparation of Gadolinium Labeled Products I, II, III or IV

Prepare a 100 ml of 20 mM solution of $GdCl_3$ in 0.2M citrate (pH 5.5). Dissolve 0.1–100 mg of products I, II, III or IV in 1–5 ml of water and place in dialysis bags with pores small enough to retain molecules larger than 10 kD. Place the dialysis bags in the Gd-citrate solution for 8–10 hours. Then substitute the Gd-citrate solution by 0.2M citrate and, finally, with 10 mM citrate-balanced saline (osmolarity is 300 mOsm). Sterile-filter or lyophilize the Gadolinium-labeled products.

Example 8

Preparation of [$^{111}$In]and Gadolinium -Labeled Products I, II, III or IV

Prepare according to the procedures of Example 4 and then transfer the dialysis bags to Gd-citrate solution as described in Example 7.

Example 9

The Purification of Labeled Products I, II, III or IV

A solution of gadolinium or [$^{111}$In] and gadolinium labeled products was prepared at 50–100 mg of polymer/ml of 5 mM sodium citrate (pH 6). Load the solution on a column of Sephadex A-25 (1×40 ml, 5 mM citrate, pH 6) and elute non-bound material with the same buffer, which has been collected, dialyzed against water, and lyophilized.

Although the above examples present general and specific guidelines for preparing and using contrast agents of this invention, one skilled in the art can assemble additional candidate molecules and compare their characteristics to those claimed by the invention.

Experimental characterization of products

Determination of size

The apparent hydrodynamic radii were determined using gel-filtration on an Ultragel AcA-34 (from LKB-IBF, France) column (1×40 ml) and LALLS (Submicron Particle Analyzer N-4MD from Coulter, Hialeah, Fla.).

Solutions of products I–IV in Gd-labeled form were prepared at 1 mg of polymer/ml and the sizes were determined by Size Distribution Processor (SDP) weight analysis at 90° angle scattering before and after the formation of Gd complexes (See Table 1). The calculation of molecular weights was based on determination of the degree of modification of PL with MPEG, as described in Example 1, assuming that on the second stage of modification all aminogroups were substituted with DTPA.

TABLE 1

Determination of size and molecular weights

| Product | diameter (LALLS) | MW (LALLS) | Apparent MW (AcA34)* | Calculated MW |
|---|---|---|---|---|
| I | 15.5 ± 1 nm | 171 kD | 200 kD | 417 kD |
| II | 16.4 ± 4 nm | 150 kD | 280 kD | 412 kD |
| III | 38.1 ± 10.5 nm | ND | >380 kD | 860 kD |
| IV | 53 ± 12 nm | ND | >380 kD | 960 kD |

Note:
*AcA 34 column was precalibrated with globular protein molecular weight markers;
ND: No Data available.

Determination of Gd content

The Gd content was determined titrametrically, (as in Korbl, J. and Pribil, R., Chemist-Analyst 45:101–103 (1956), or by plasma emission spectroscopy (from Gallbraith Labs, Knoxville Tenn.). The Gd content did not exceed 13.18% by weight (0.8 mmol Gd/g polymer, product I). Typically products II, III, and IV contained ca. 5% Gd by weight (0.32 mmol Gd/g polymer).

Measurement of relaxivity values (R1 and R2)

Determination of relaxation times of the $H_2O$ protons was performed using a Minispec (IBM PC/20) pulsed NMR spectrometer at 20 MHz, 38° C. Gd-labeled products were appropriately diluted with CBS and T1 and T2 parameters were measured. Inversion recovery and CPMG pulse sequences were used to determine T1 and T2 values, respectively. The concentration dependencies of relaxation rates 1/T1 and 1/T2 were plotted and fitted using linear regression (r=0.99). R1 and R2 values were determined as slope values (See Table 2).

TABLE 2

Molecular and atomic relaxivities

| Product | R1 | R2 | R1/Gd | R2/Gd | [mMol-1 s-1] |
|---|---|---|---|---|---|
| I | 5061 | 5053 | 18.1 | 16.9 | |
| II | 2076 | 2035 | 17.6 | 17.1 | |
| IV | 4565 | 6547 | 18.5 | 19.0 | |

Calculated values of molecular weights of Gd-labeled products were used for molecular relaxivity determinations.

Graft Co-Polymer Adducts

Synthetic Method Overview

Graft-co-polymers of the invention include a central carrier chain, a protecting group, and, optionally, a reporter group. Each group is linked together and is capable of forming reversibly linkages with a platinum(II) compound. A reversible linkage between the graft co-polymer and a platinum(II) compound includes, but is not limited to 1) the formation of hydrogen bonds, 2) the formation of bonds with aguated platinum(II) compounds, 3) the formation of coordination bonds with the platinum atom (charged or neutral) and 4) electrostatic interactions, particularly with chemical groups of the graft co-polymer which include a carbonyl group, for example carboxylic acid groups. The chemical bonds formed between platinum (II) compounds and amino acids have been investigated (Appleton and Hall *J. Chem. Soc. Commun.* 493 911 (1983) and references therein). The platinum(II) compound may be present as an electroneutral and/or positively charged (aquated) form.

Figure 12:
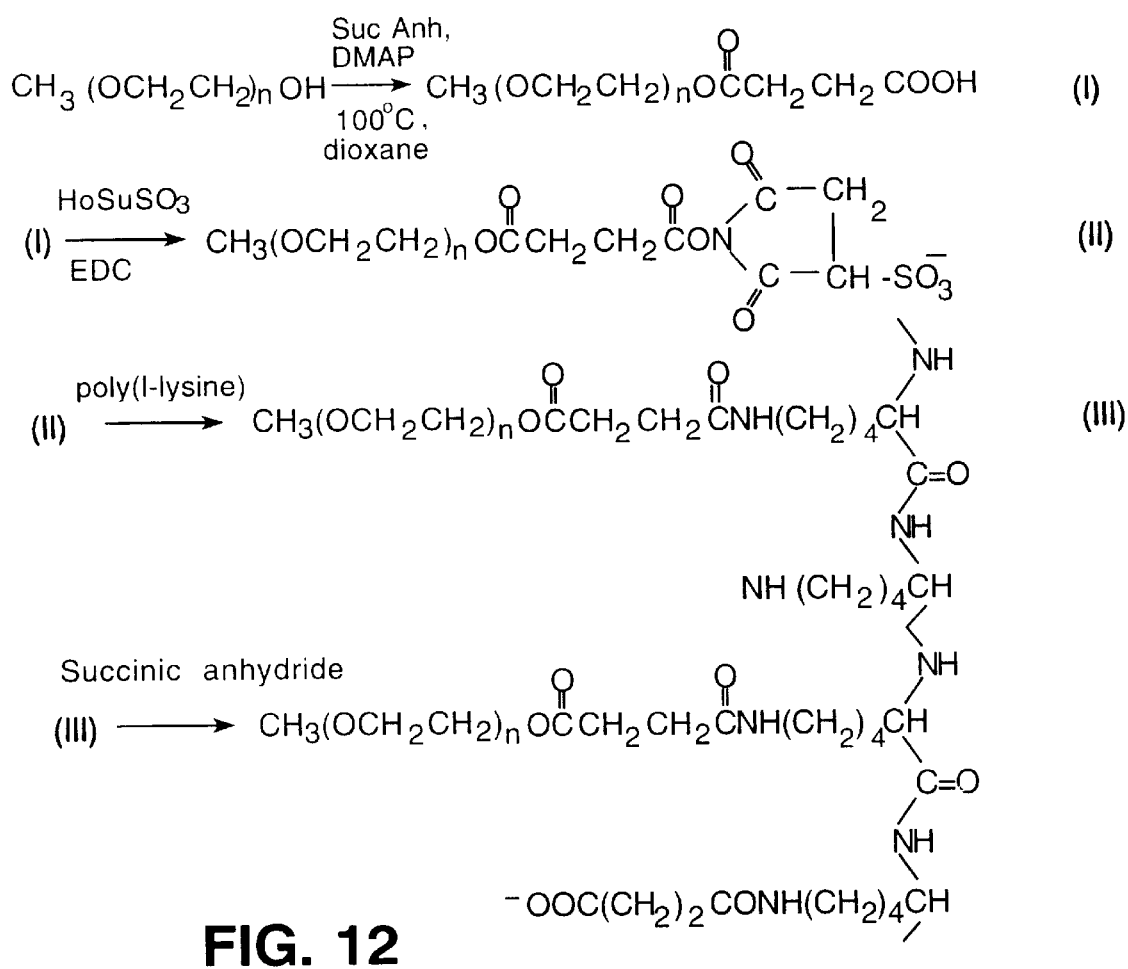
FIG. 12 is a drawing outlining the chemical synthesis of the graft-co-polymer, poly[([N-(methoxy poly(ethylene) glycol)-o-succinyl]-l-lysyl)n-(N-succinyl-l-lysyl)m]lysine (i.e., MPEG-Poly(L-lysine)succinate or MPEG-PL-succinate).

The synthesis of a graft-co-polymer adduct from a polymeric carrier containing amino groups generally involves three synthetic stages: 1) covalent modification of a backbone carrier with protective chains; 2) modification of the product with negatively charged groups, for example, modification with succinic acid; and 3) incubating the co-polymer and the platinum(II) compound together to achieve formation of a graft co-polymer adduct (see FIGS. 12 and 13). Preparation of an adduct by starting with negatively charged polymeric carrier does not include modification with negatively charged groups and thus includes only the first and third stage.

As outlined in FIG. 12 a graft-co-polymer was prepared by obtaining a carboxylated derivative of methoxy poly (ethylene glycol)(MPEG) (I), and reacting it with sulfosuccinimide in the presence of carbodiimide (II) reacting polyamino acid with activated MPEG analogs (III), and then reacting this mixture with an excess of dicarboxylic acid anhydride. This procedure was preferred when poly-l-lysine was used as the backbone. The nucleophilic epsilon-amino groups of poly-l-lysine were also reacted with activated derivatives of carboxylated MPEG, e.g., acid chlorides, anhydrides, mixed anhydrides, nitrenes, isothiocyanates and imidazolides, activated esters, e.g hydroxysuccinimide, hydroxysulfosuccinimide, p-nitrophenyl, benzotriazolide (not shown). The dicarboxylic acid used can be in activated form, e.g., anhydride, mixed anhydride, isothiocyanate, succinimide or sulfosuccinimide. The preferred carboxylic acid is dicarboxylic acid although a dicarboxylic acid of the general formula of X—(CH2)nCOOH where X=I,Br,CL or F and n=1–10 can also be used. The reaction may be preceded with additional chemical modification of the polyamino acid backbone. Finally, the sequence of chemical linking of protective chains and an agent to a polymeric carrier may be reversed, i.e. linking of an acid preceeds linking of protective chain(s) to a polymeric carrier.

As outlined in FIG. 12, the first stage of synthesis resulted in the formation of a graft-co-polymer where approximately 15–30% of monomeric residues of the polymeric carrier here modified with protective chains. The second and third stages yielded a graft co-polymer where generally all monomeric residues that were not linked to protective chains were modified with negatively charged moieties. The fourth stage (FIGS. 13A and 13B) generally yielded a product having more than 0.1% of platinum by weight. Generally, the adduct product had between 1% and 30% platinum by weight, inclusive, the majority of platinum (more than 50% of total content) being capable of dissociating from the graft co-polymer.

The graft co-polymer (i.e., without a reversibly bound platinum(II) compound) has a molecular weight between 50 and 1500 kDa. Generally, the molecular weight of the adduct (i.e., graft co-polymer and cDDP) is between 50 and 1500 kD, inclusive, the graft co-polymer adduct may be purified in a form which elutes as a single peak on a standard size-exclusion column.

Synthesis of a Graft Co-polmyer

Graft co-polymers of the invention may be synthesized using the following methods. The synthesis of the graft co-polymer poly[([N-(methoxy poly(ethylene)glycol)-o-succinyl]-l-lysyl)n-(N-succinyl-l-lysyl)m]lysine includes poly-l-lysine, as an examplary polymeric carrier, methoxypolyethyleneglycol as an examplary protective chain, and succinate as an examplary reporter group. Preparation of the graft co-polymer adduct proceeds by incubation of cDDP with the graft co-polymer in water or water/DMF mixtures. cDDP binds spontaneously to the graft co-polymer. A graft co-polymer adduct is especially suitable as a macromolecular contrast agent.

Example 10

1. Synthesis of monomethoxy poly(ethylene glycol) succinate: 75 g (15 mmol) of methoxy(poly(ethylene) glycol)5000 was dissolved in 200 ml of dioxane (freshly redistilled), add 7.9 g (75 mmol) of succinic anhydride. 1.9 g (15 mmol) of 4-dimethylaminopyridine was added in 200 ml of dioxane. The mixture was refluxed under nitrogen with stirrring in a 2-necked flask for 3 hrs at 100° C. After 24 hrs another portion of 8 g succinic anhydride was added, then 2 g of 4 dimethylaminopyridine in 100 ml of dioxane was added. The combination was mixed at 100° C. for an additional 4 hrs under nitrogen. The reaction mixture was cooled to 60° C. and transferred to an apyrogenic 1-neck 1 L flask. Dioxane was removed by using a rotary evaporator, mixing the residue with 200 ml of chloroform, filtering through glass fiber filters, and cooling on ice and filter again. Chloroform was removed at 40° C. on rotary evaporator, then, 300 ml of ethanol was added to the residue. 4 g of activated charcoal was added and the solution boiled with a reflux for 1 h. The mixture was filtered, then 300 ml of ethyl acetate was added to the mixture; the mixture was then left at 4° C. for 24 h. Afterwords, the was filtered and the precipitate saved. The precipitate was dissolved in 800 ml of ethyl alcohol and mixed with 100 g of ethanol-washed AG50 W-X8 resin. The resin was filtered and concentrated by using a rotary evaporator. 400 ml of ethyl acetate was added and the material transfered into Erlenmeyer flasks and kept at −10° C. for 4 hrs. The resulting material was filtered and the precipitate dried in a vacuum. The weight of the resulting product was 44 g. The yield of purified MPEG-succinate was 57% of theoretical yield.

| Chemical analysis | | |
|---|---|---|
| Element | Calculated* (%) | Determined (%) |
| C | 54.34 | 53.78 |
| O | 36.7 | 37.09 |
| H | 9.02 | 9.07 |

*Calculated using a brutto formula: $C_{231}H_{460}O_{117}$

Example 11

1. Synthesis of MPEG5000-PL-DTPA:

0.1M carbonate buffer was prepared by dissolving 4.2 g of sodium bicarbonate in water, after which, 20 µl of 50% NaOH solution was added. The solution was filtered through a sterile 0.4 µm filter. A solution was prepared of 1 g of poly-l-lysine/175 ml of 0.1M carbonate buffer and 50 µl was withdrawn for amino group determination. 9.6 g of MPEG-succinate was dissolved in 25 ml of sterile apyrogenic water and 500 mg of N-hydroxysulfosuccinimide was added, followed by 1 g of 1-(3-dimethyl aminopropyl)-3-ethyl carbodiimide, hydrochloride. The solution of MPEG-succinate was activated at room temperature for 10 min. The solution of activated MPEG-succinate N-hydroxy(sulfo) succinimide ester was transferred to the poly-l-lysine solution and incubated for 4 hrs at room temperature with mixing. A 50 µl aliquot was removed for amino group determination. Amino groups were determined by trinitrobenzene sulfonic acid (TNBS) titration. The assay for aminogroups gave 20–25% of amino group substitution in comparison to initial poly-l-lysine.

1 g of succinic anhydride was dissolved in 10 ml of dimethylsulfoxide and added to the reaction mixture dropwise. The pH was kept at 8 by the addition of a 5N NaOH solution. The reaction mixture was stirred for 4 hrs at room temperature. The solution was filtered through a sterile apyrogenic membrane and diluted with 100 ml of sterile apyrogenic water and transfered into a 300ml diafiltration cell equipped with a YM100 membrane. The cell was pressurized by using a nitrogen source and concentrated to 30 ml at 25 psig. The contents were diluted with sterile apyrogenic water to 300 ml and concentrated again. The procedure (i.e. concentration/dilution) was repeated 4 times (total of 5 cycles). The purity of the sample was analyzed by using size-exclusion HPLC (SEC-%, 4×25 cm, Rainin Instru. Co.). The solution was transferred to an autoclaved lyophilization flask and frozen in liquid nitrogen and lyophylized.

| Element | Calculated* (%) | Determined (%) |
|---|---|---|
| C | 53 | 48.68 |
| O | 35.7 | 35.67 |
| H | 7.8 | 8.8 |
| N | 3.0 | 4.96 |

*Calculated using a brutto formula: $C_{25360}O_{12630}N_{1200}H_{44460}$

Example 12

1. Synthesis of PL-succinate: A solution of 1 g of poly-l-lysine/175 ml of 0.1M carbonate buffer was prepared and a 50 µl aliquot was withdrawn for amino group determination. 1 g of succinic anhydride was added and dissolved in 10 ml of dimethylsulfoxide, which was added to the reaction mixture dropwise. The pH was kept at 8 by addition of a 5N NaOH solution. The reaction mixture was stirred for 4 hrs at room temperature. A 50 µl aliquot was removed for amino group determination. The amino groups were determined by trinitrobenzene sulfonic acid (TNBS) titration. The assay for amino groups gave 100% of amino group substitution in comparison to the initial poly-l-lysine.

The solution was filtered through a sterile apyrogenic membrane. The solution was diluted with 100 ml of sterile apyrogenic water and transfered into a 300ml diafiltration cell equipped with a YM100 membrane. The cell was pressurized by using a nitrogen source and concentrated to 30 ml at 25 psig. The contents were diluted with sterile apyrogenic water to 300 ml and concentrated again. The procedure (i.e. concentration/dilution) was preformed 4 times for a total of 5 cycles. The purity was analyzed by using size-exclusion HPLC. The solution was transferred to an autoclaved lyophilization flask, frozen in liquid nitrogen and lyophylized.

Example 13

1. Synthesis of [$^{111}$In]-DTPA labeled graft-co-polymers: MPEG-PL or PL was prepared as disclosed in Example 11.

Before succinic anhydride was added, a solution of cyclic anhydride of DTPA in DMSO was added at the ratio of 5 mol DTPA per 1 mol of polymer. The mixture was incubated for 1 h at room temperature, pH 7.5. Then, an excess of succinic anhydride was added to block the remaining amino groups. The succinylated product was purified by ultrafiltration as in Example 11. [$^{111}$] chloride was mixed with the solution of purified graft co-polymer, which, prior to mixing, was dissolved in 20 mM sodium citrate, pH 5.5.

Example 14

1. Preparation of a cDDP adduct with MPEG-PL-succinate or PL-succinate:

i) Aqueous Solution: A solution of MPEG-PL-succinate or PL-succinate was prepared in water at a concentration of 20 mg/ml. A suspension of 12 mg/ml cDDP was dissolved in water. 1 ml of the cDDP solution was combined with 1 ml of polymer solution and stirred overnight at 40° C. Any unsolubilized cDDP was removed by filtration. In order to purify the adduct, the mixture was loaded onto a spin-column filled with Sephadex G-25 m (10×1 cm). The eluate was collected after centrifuging at 800 g for 5 min. The non-bound cDDP was determined by a standard o-phenylenediamine assay Schechter et al., *Cancer Immunol. Immunother* 25, 225 (1987). The total amount of platinum in the adduct was determined by plasma adsorption spectroscopy.

ii) Water/Organic Solution: A solution of MPEG-PL-succinate or PL-succinate was prepared in water at 100 mg/ml. A suspension of 16.5 mg/ml cDDP was prepared in dimethylformamide. 1 vol of the cDDP solution was combined with 3 vol of polymer solution and incubated overnight at 40° C. 2 vol of water was subsequently added. The mixture was loaded onto a spin-column filled with Sephadex G-25 m (10×1 cm) and the eluate collected after centrifuging at 800 g for 5 min. The amount of non-bound cisplatinum was determined by o-phenylenediamine assay. The amount of total platinum was determined by plasma adsorption spectroscopy.

The effectiveness of MPEG-PL-succinate as a carrier for cDDP, was evaluated by quantitative HPLC analysis of adducts formed after the addition of cDDP at several concentrations. Insolubility of cDDP-adducts was not observed even at cDDP/succinate ratios as high as 12:1. Scatchard analysis obtained by integration of cDDP the elution peaks indicated that MPEG-PL-succinate has approximately 1700 individual binding sites for cDDP, 25% of which are represented with high-affinity sites (Kd, apparent=$3.6 \cdot 10^{-5}$ M$^{-1}$) and 75%—with low affinity (Kd,apparent=$2 \cdot 10^3$M$^{-1}$), (FIG. 14). The calculated cDPP/succinate ratio (8.5:1) in the purified adduct indicates that linkages between the protonated amino groups of cDDP (or cis-aq) and carboxylic groups of the graft co-polymer, as well as other non-covalent linkages, are present in the adduct. The data indicate that the protective chain is involved in the stabilization of cDDP with the polymeric backbone.

Dissociation of the cDDP from the graft co-polymer was detected by dialysis against isotonic saline or against isotonic medium containing 10 g/l of serum albumin (FIG. 15). The latter experiment was designed to mimic the presence of plasma proteins in the bloodstream of a mammal. Plasma proteins, are capable of irreversible (i.e., covalent) binding of free (i.e., non-complexed) cDDP. cDDP was released from the carrier with the half-time of 63 h in saline. In the presence of serum albumin, 20% of the cDDP was released at a fast rate (half-time-4 min), but the major fraction of the drug was released slowly with a half-time of 83 h. This result clearly demonstrates that the adduct is capable of slow cDDP release for prolonged periods of time in the bloodstream.

Example 15

1. Cytotoxicity of the graft co-polymer adduct in vitro:

Human mammary adenocarcinoma cells (BT-20 cells) were plated in 96-well plates in medium (i.e. 10% FCS, DMEM) at a cell density of 350,000 cells/well. Free cDDP, a cDDP graft co-polymer adduct or cDDP linked to PL-succinate were each diluted serially with cell medium and incubated with the cells overnight at 37° C. Cytotoxicity was determined by a standard [$^3$H]methylthymidine DNA incorporation assay. For example, 10 μCi of [$^3$H] methylthymidine were added per well and incubated with the cells for 3 hours. The cells were collected by harvesting on glass fiber membranes. The amount of bound radioactivity was determined on each membrane by standard scintillation counting.

Both MPEG-PL-succinate/cDDP and free cDDP showed pronounced cytotoxic effects by inhibiting DNA synthesis in human mammary adenocarcinoma cells after 16 h incubation (FIG. 16). At concentrations lower than 0.5 μM, MPEG-PL-succinate-cDDP showed higher cytotoxicity than an adduct obtained with succinylated poly-l-lysine, i.e. with a polymeric carrier devoid of protective chains. Concentrations of adduct showing about 50% inhibition of cell proliferation were: 0.9 μM for PL-succinate-cDDP, 0.7 μM for MPEG-PL-succinate-cDDP and 0.3 μM for the free cDDP.

Example 16.

1. Determination of the biodistribution of [$^{111}$In]-polymers in rats: R3230 or NF tumors were each implanted in the flank region of female Fisher rats (250 g). After formation of palpable tumors (about 10 days, tumor size is approximately 0.4–0.6 g) animals (n=3/time point) were injected i.v. with 60 mcCi of [$^{111}$In]-labeled MPEG-PL-succinate (40 mg polymer/kg). The biodistribution of the co-polymer was determined in the major organs at 24 and 96 hr post-injection (FIG. 17).

MPEG-PL-succinate-cDDP adduct exhibited a long circulation time in the bloodstream, whereas PL-succinate-cDDP did not. 24 h after i.v. injection of the DTPA-labeled co-polymer, 40% of it was found in the blood, whereas only 1% the MPEG-free adduct remained in blood. After 96 h, most (>80%) of MPEG-PL-succinate-cDDP adduct had been removed from circulation. MPEG-free adducts accumulated in kidneys (15.0±1.2% dose/g), whereas acumulation of MPEG-PL-succinate-cDDP was 5 fold lower (3.5±0.5% dose/g). Accumulation of MPEG-containing adduct in rat adenocarcinomas was 4–5 fold higher (2.6±0.3% dose/g (NF tumor); 2.05±0.25% dose/g (R3230 tumor) than MPEG-free adducts (0.5% dose/g).

These in vivo experiments demonstrate that MPEG-PL-succinate/cDDP adduct has an advantageous pharmacological profile in terms of: 1) longer circulation in the blood stream; 2) lower accumulation in kidneys (lower chance of eliciting of nephrotoxicity) and; 3) higher accumulation in solid tumors. Targeting of cDDP to the tumor could not be achieved with an adduct that included a polymer devoid of protective chains.

MPEG-PL-succinate was shown to be a high-capacity carrier for cDDP. cDDP is a highly potent chemotherapeutic agent, one which nonetheless exhibits significant systemic toxicity. Prolonged blood circulation of the adduct creates a circulating depot of reversibly bound cDDP. The high cytotoxicity of the drug in vitro and in vivo indicates that graft co-polymer adducts which include a platinum(II) compound, particularly cDDP will be useful therapeutic agents in the treatment of human cancer. Furthermore, the data suggest that graft co-polymer adducts which include a platinum(II) compound can be administered either alone or in combination with other chemotheraputic agents in order to treat human cancer.

The art-skilled will understand that an adduct consisting of a graft co-polymer and a platinum(II) compound other than cDDP can be made by following the above-described methods, except that the platinum(II) compound will be substituted for cDDP. Generally, the amount of platinum(II) compound that can be combined with a graft co-polymer is within the range disclosed for cDDP. The amount of platinum(II) compound associated with a graft-co-polymer can be assayed by plasma absorption spectroscopy and the adduct can be purified and tested by any of the in vitro or in vivo methods disclosed herein.

Administration of Graft Co-Polymer Adducts

The adducts provided herein can be administered either alone or formulated into pharmaceutical compositions by admixture with pharmaceutically acceptably nontoxic excipients and carriers.

An adduct of the invention may be prepared for use in parenteral administration, particularly in the form of liquid solutions or suspensions; for oral administration, particularly in the form of tablets or capsules; or intranasally, particularly in the form of powders, nasal drops, or aerosols.

An adduct of the invention may be conveniently administered in unit dosage form and may be prepared by any of the methods well known in the pharmaceutical art, or example, as described in *Remington's Pharmaceutical Sciences* (Mack Pub. Co., Easton, Pa., 1980). Formulations for parenteral administration of an adduct of the invention may include as common excipients sterile water or saline, polyalkylene glycols such as polyethylene glycol, oils of vegetable origin, hydrogenated naphthalenes and the like. Formulations for parenteral administration may also include glycocholate for buccal administration, methoxysalicylate for rectal administration, or citric acid for vaginal administration.

An adduct of the invention can be employed as the sole active agent in a pharmaceutical or can be used in combination with other chemotherapeutic agents such as cDDP, carboplatin, doxorubicin, or cyclophosphamide. In particular, the chemotherapeutic agent may be provided as a biocompatible, biodegradable lactide polymer, lactide/glycolide co-polymer, or polyoxyethylene-polyoxypropylene co-polymers, each of which may serve as useful adjuncts to therapy. Other useful excipients to control the release of the chemotherapeutic agent include parenteral delivery systems such as ethylene-vinyl acetate co-polymer particles, osmotic pumps, implantable infusion systems, and liposomes.

The concentration of an adduct of the invention described herein in a therapeutic composition will vary depending upon a number of factors, including the adduct to be administered, the chemical characteristics (e.g., hydrophobicity) of the adduct employed, and the route of administration. In general terms, an adduct of the invention may be provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the cancer, the overall health status of the particular patient, the relative biological efficacy of the adduct selected, the formulation of the compound excipients, and its route of administration, and whether a chemotherapeutic drug is chosen for adjunctive therapy.

All publications and patent applications mentioned in the specification are indicative of the level of skill of those in the art to which this invention pertains. All publications and patent applications are incorporated herein by reference to the same extent as if each individual publication or patent application were specifically and individually stated to be incorporated by reference.

Although the foregoing invention has been described in some detail by way of illustration and example for the purposes of clarity of understanding, one skilled in the art will easily ascertain that certain changes and modifications may be practiced without departing from the spirit and scope of the appended claims.

Other embodiments are within the following claims:

What is claimed is:

1. A biocompatible platinum-carrying adduct, comprising:
   (i) a polymeric carrier;
   (ii) a plurality of polymeric protective side chains, wherein said plurality corresponds to a number between 15% and 30%, inclusive, of the number of monomeric units in the polymeric backbone; and wherein each protective side chain, independently,
      (a) is covalently linked to said backbone,
      (b) has a molecular weight between 500 and 10,000 Daltons, and
      (c) comprises a polyethylene glycol derivative; and
   (iii) a plurality of platinum-carrying side groups, wherein each platinum-carrying side group, independently,
      (1) is covalently linked to said backbone,
      (2) is dissociably linked to a platinum (II) compound, and
      (3) has a molecular weight independently less than 465 Daltons, exclusive of said platinum (II) compound.

2. The adduct of claim 1, wherein said adduct further comprises a reporter group linked to said polymeric carrier or to said polymeric carrier and said protective chain.

3. The adduct of claim 1, wherein said polymeric carrier is chosen from the group consisting of polyamino acids, polyethyleneimines, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, and carboxymethylated oligosaccharides.

4. The adduct of claim 3, wherein said polyamino acid has 20–560 amino acid units.

5. The adduct of claim 4, wherein said polyamino acid has a molecular weight of 1,000–100,000 daltons.

6. The adduct of claim 3, wherein said polyamino acid is a polymer of a single species of amino acid.

7. The adduct of claim 3, wherein said polyamino acid is a polymer of at least two different species of amino acids.

8. The adduct of claim 3, wherein said polyamino acid is a block co-polymer.

9. The adduct of claim 3, wherein said polyamino acid comprises polyamino acid fragments linked by cleavable bonds.

10. The adduct of claim 9, wherein said cleavable bonds are S—S bonds.

11. The adduct of claim 3, wherein said polyamino acid is poly-l-lysine, poly-d-lysine, poly-alpha,beta-(2-aminoethyl)-D,L aspartamide, poly-l-aspartic acid or poly-glutamic acid.

12. The adduct of claim 3, wherein said polyamino acid is non-proteinaceous.

13. The adduct of claim 1, wherein said protective chain is polyethylene glycol, polypropylene glycol, a co-polymer of polyethylene glycol and polypropylene glycol; or a monoesterified derivative thereof.

14. The protective chain of claim 13, wherein said monoesterified derivative is methoxypolyethylene glycol, methoxypolypropylene glycol, or a co-polymer of methoxypolyethylene glycol and methoxypolypropyleneglycol.

15. The adduct of claim 1, wherein said protective chain is polyethylene glycol monoamine, methoxypolyethylene glycol monoamine, methoxy polyethylene glycol hydrazine, methoxy polyethylene glycol imidazolide or a polyethylene glycol diacid.

16. The adduct of claim 1, wherein said protective chain is a block co-polymer of polyethylene glycol and one of the group of polyamino acids, polysaccharides, polyamidoamines, polyethyleneamines, or polynucleotides.

17. The adduct of claim 1, wherein said protective chain is a co-polymer of polyethylene glycol comprising a monoester of a dicarboxylic acid.

18. The adduct of claim 2, wherein said reporter group is a complexone.

19. The adduct of claim 18, wherein said complexone is a chelating group.

20. The adduct of claim 19, wherein said chelating group is diethylenetriamine-pentaacetic acid, triethylenetetraminehexaacetic acid, ethylenediaminetetraacetic acid, 1,2-diaminocyclo-hexane-N,N,N',N'-tetraacetic acid, N,N'-Di (2-hydroxybenzyl)ethylenediamine, N-(2-hydroxyethyl) ethylenediaminetriacetic acid, nitrilotriacetic acid, ethylenebis(oxyethylenenitrilo) tetraacetic acid, 1,4,7,10,-tetraazacyclododecane-N,N',N", N'"-tetraacetic acid, 1,4,7, 10,-tetraazacyclododecane-N,N',N", -triacetic acid, 1,4,7-tris(carboxymethyl)-10-(2'-hydroxy)propyl)-1,4,7,10-tetraazocyclodecane, 1,4,7-triazacyclonane-N,N',N"-triacetic acid, or 1,4,8,11-tetraazacyclotetradecane-N,N',N", N'"-tetra-acetic acid.

21. The adduct of claim 2, wherein said reporter group comprises a diagnostic agent.

22. The adduct of claim 21, wherein said diagnostic agent is a contrast agent.

23. A biocompatible graft co-polymer adduct comprising:
a polymeric carrier;
a protective chain linked to said polymeric carrier;
a platinum(II) compound reversibly linked to said polymeric carrier and said protective chain; and,
a contrast agent comprising a paramagnetic element linked to said polymeric carrier or to said polymeric carrier and said protective chain.

24. The adduct of claim 23, wherein said paramagnetic element is chosen from the group of transitional metals or lanthanides having atomic numbers 21–29, 42, 44, or 57–71.

25. The adduct of claim 23, wherein said paramagnetic element is gadolinium (III), dysprosium (III), holmium (III), europium (III), iron (III), or manganese (II).

26. The adduct of claim 18, further comprising an alpha-, beta-, or gamma-emitting radionuclide linked to said complexone.

27. The adduct of claim 26, wherein said radionuclide is gallium 67, indium 111, technetium 99m, chromium 51, cobalt 57, molybdenum 99, or a molecule linked to an iodine isotope.

28. The adduct of claim 22, wherein said contrast agent comprises a superparamagnetic element.

29. The adduct of claim 23, wherein said contrast agent further comprises a radionuclide.

30. The adduct of claim 2, wherein said reporter group comprises a therapeutic agent.

31. The adduct of claim 30, wherein said therapeutic agent is a cytostatic, antibiotic, hormonal, analgesic, psychotropic, anti-inflammatory, antiviral, or antifungal drug, or a lymphokine.

32. The adduct of claim 2, wherein said reporter group is a particle, colloidal particle, or a colloidal precipitate.

33. The adduct of claim 32, wherein said colloidal precipitate includes an oxide, sulfide, or hydroxide of a transitional element or lanthanide having atomic numbers 21–29, 42, 44, or 57–71.

34. The adduct of claim 2, wherein said reporter group is a silicon oxide colloid or polymer containing silicon, sulfur, or carbon.

35. The adduct of claim 2, wherein said reporter group has the general formula —COOH or —$(CH_2)_p$COOH, where p is between 1 and 7, inclusive.

36. The adduct of claim 35, wherein said reporter group is —$CH_2CH_2COOH$.

37. The adduct of claim 1, wherein said platinum(II) compound has the general formula:

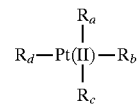

wherein:
a) each $R_a$, $R_b$, $R_c$, $R_d$ independently is —$OH_2$, Cl, Br, I, —$NH_2$, or —$N(R_e)_2$, where each $R_e$ independently is H, lower alkyl, or lower cycloalkyl, with the proviso that both of $R_e$ are not H; and each $R_a$, $R_b$, $R_c$, and $R_d$ is the same or different;

or b) $R_a$ and $R_d$ are combined to form a linking group of the formula: —$NH(CH_2)_{p2}NH$—, where p2 is 1 or 2; —O—CO—C$(CH_2)_{p3}$—CO—O—, where p3 is between 4 and 6, inclusive;

—NH—$(C_6H_{10})$—NH—; or —O—CO—$(CH_2)_{p4}$—CO—O—, where p4 is between 1 and 6, inclusive; and $R_b$, and $R_c$ are as defined in a);

or c) $R_a$ and $R_d$, $R_b$ and $R_c$, are each independently combined to form a linking group of the formula: —NH$(CH_2)_{p2}$NH—, where p2 is 1 or 2; —O—CO—C$(CH_2)_{p3}$—C—CO—O—, where p3 is between 4 and 6, inclusive;

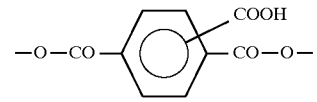

—NH—$(C_6H_{10})$—NH—; or —O—CO—$(CH_2)_{p4}$—CO—O—, where p4 is between 1 and 6, inclusive; and each $R_a$ and $R_d$, $R_b$ and $R_c$, is the same or different.

38. The adduct of claim 1, wherein said platinum(II) compound is any one of cDDP, cis-aq, carboplatin, iproplatin, DACCP, malonatoplatinum, trans (±)-1,2-cylcohexanediammineplatinum (II), cis-DEP, or Pt(II)(NH$_3$)(RNH$_2$)Cl$_2$, where R is H, methyl, ethyl, isopropyl, cyclopropyl, cyclobutyl, cyclopentyl, or cylcohexyl.

39. The adduct of claim 1, wherein said adduct comprises between 0.1% and 30% (w\w), inclusive, of platinum.

40. The adduct of claim 39, wherein said adduct exhibits a molecular weight of between 50 and 1500 kDa, inclusive.

41. The adduct of claim 36, wherein said graft co-polymer is poly[([N-(methoxy poly(ethylene)glycol)-o-succinyl]-l-lysyl)n-(N-succinyl-l-lysyl)m]lysine and exhibits a molecular weight of between 1500 and 150,000 daltons, inclusive; said succinate and said Pt(II) compound being present in a molar ratio of between 1:1 and 1:20 (inclusive), respectively.

42. The adduct of claim 40, wherein said platinum(II) compound is cDDP.

43. The adduct of claim 2, wherein said linked polymeric carrier, polymeric protective side chains and reporter group has the general formula:

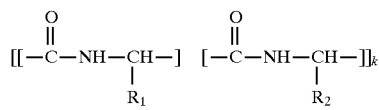

wherein said

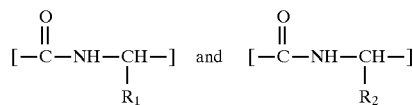

groups can be linked in any order and k is 100–560; and a) R$_1$ is (CH$_2$)$_4$NHCO(CH$_2$)$_n$COOCH$_2$CH$_2$A—B—OR$_3$, where n is 2–6; A is [OCH$_2$CH$_2$]$_x$, where x is 15–220; B is [OCH$_2$CH$_2$]$_x$ or [OCH(CH$_3$)CH$_2$]$_y$, where y+x is 17–220; R$_2$ is a chelating group; and R$_3$ is H, (CH$_2$)$_y$CH$_3$ or (CH$_2$)$_y$COOH, where y is 0–7;

or b) R$_1$ is —CH$_2$(R$_g$)NHCO (CH$_2$)$_{n1}$COO((CH$_2$)$_{n2}$O)$_{n3}$CH$_3$, where R$_g$ is —CH$_2$CH$_2$CH$_2$—, —CO— or —CH$_2$CO—; n1 is 2 to 6, inclusive; n2 is 2 or 3; n3 is 10–250, inclusive; and R$_2$ is —CH$_2$(R$_g$)NHCOR$_h$, where R$_h$ is —COOH or —(CH$_2$)$_{y2}$COOH, where y2 is 1 to 7, inclusive.

44. The adduct of claim 43, wherein said chelating group is diethylenetriamine pentaacetic acid, 1,4,7,10,-tetraazacyclododecane-N,N',N'',N'''-tetraacetic acid, 1,4,7,10,-tetraazacyclododecane-N,N',N'',-triacetic acid, ethylene-bis(oxyethylenenitrilo)tetraacetic acid, or ethylenediaminetetraacetic acid.

45. The adduct of claim 2, wherein said reporter group is a pyridiyldithioacyl group, or a diazo- or hydrazo-group.

46. The adduct of claim 45, wherein said pyridyldithioacyl group is a N-(2-pyridyldithio)propionyl group, N-hydroxysuccinimidyl, N-hydroxysulfosuccinimidyl, imidazolyl, benzotriazolyl, aminoalkyl, aldehyde, thioalkyls, thiolane, haloid acyl, haloid alkyl, or haloid phenyl.

47. The adduct of claim 45, wherein said diazo- or hydrazo-group is 4-hydrazionoxyethyl, 4-hydrazinobenzyl, diasirinyl, azidophenyl, or azidoalkyl groups.

48. The adduct of claim 2, wherein said reporter group is a fluorine-containing molecule.

49. The adduct of claim 39, wherein said platinum(II) compound is cDDP.

* * * * *